United States Patent [19]

Olivera et al.

[11] Patent Number: 5,633,347

[45] Date of Patent: May 27, 1997

[54] CONOTOXIN PEPTIDES

[75] Inventors: Baldomero M. Olivera; Lourdes J. Cruz; David R. Hillyard; J. Michael McIntosh, all of Salt Lake City, Utah; Ameurfino O. Santos, Quezon City, Philippines

[73] Assignee: University of Utah Research Foundation, Salt Lake City, Utah

[21] Appl. No.: 480,750

[22] Filed: Jun. 7, 1995

Related U.S. Application Data

[63] Continuation-in-part of Ser. No. 137,800, Oct. 19, 1993, Pat. No. 5,514,774, which is a continuation-in-part of Ser. No. 84,848, Jun. 29, 1993, Pat. No. 5,432,155.

[51] Int. Cl.$^6$ .................................................. C07K 14/435
[52] U.S. Cl. ........................... 530/324; 530/300; 530/857
[58] Field of Search ..................................... 530/300, 324, 530/326, 325

[56] References Cited

U.S. PATENT DOCUMENTS

| 4,447,356 | 5/1984 | Olivera et al. | 530/327 |
| 5,041,389 | 8/1991 | Lindstrom | 436/518 |

OTHER PUBLICATIONS

Cattaneo, M.G. et al. (1993). "Nicotine Stimulates a Serotonergic Autocrine Loop in Human Small–Cell Lung Carcinoma," *Cancer Res.* 53:5566–5568.

Chini, B. et al. (1992). "Neuronal–type α–bungarotoxin receptors and the α$_5$–nicotinic receptor subunit gene are expressed in neuronal and nonneuronal human cell lines," *Proc. Natl. Acad. Sci. USA* 89:1572–1576.

Codignola, A. et al. (1994). "Serotonin release and cell proliferation are under the control of α–bungarotoxin–sensitive nicotinic receptors in small–cell lung carcinoma cell lines," *FEBS Lett.* 342:286–290.

Fambrough, D.M. et al. (1973). "Neuromuscular Junction in Myasthenia Gravis: Decreased Acetylcholine Receptors," *Science* 182:293–295.

Maneckjee, R. and Minna, J.D. (1990). "Opioid and nicotine receptors affect growth regulation of human lung cancer cell lines," *Proc. Natl. Acad. Sci. USA* 87:3294–3298 (1990).

Olivera, B.M. et al. (1984). "Purification and Sequence of a Presynaptic Peptide Toxin from Conus geographus Venom," *Biochemistry* 23:5087–5090.

Schüller, H.M. et al. (1990). "Nicotine, Acetylcholine and Bombesin are trophic Growth Factors in Neuroendocrine Cell Lines Derived from Experimental Hamster Lung Tumors," *Life Sciences* 47:571–578.

Tarroni, P. et al. (1992). "Neuronal–type nicotinic receptors in human neuroblastoma and small–cell lung carcinoma cell lines," *FEBS Lett.* 312:66–70.

*Primary Examiner*—Robert A. Wax
*Assistant Examiner*—G. E. Bugaisky
*Attorney, Agent, or Firm*—Venable, Baetjer, Howard & Civiletti, LLP

[57] ABSTRACT

The invention is directed to A-lineage conotoxin peptides, which are conotoxin peptides that have strong homology in the signal sequence and the 3'-untranslated region of the genes coding for these peptides to the sequences in the α-conotoxin peptides. The A-lineage conotoxin peptides include the α-conotoxin peptides, the α-conotoxin-like peptides and the κ-conotoxin peptides, described further below. The α-conotoxin-peptides generally share a "core" sequence motif. This core sequence is termed the α3/5 core and is represented as Cys-Cys-Xaa-Xaa-Xaa- Cys-Xaa-Xaa-Xaa-Xaa-Xaa-Cys (SEQ ID NO:1). The α-conotoxin-like peptides generally share a core sequence termed the α4/7 core and is represented as Cys-Cys-Xaa-Xaa-Xaa-Xaa-Cys-Xaa-Xaa-Xaa-Xaa-Xaa-Xaa-Xaa-Cys (SEQ ID NO:2). The κ-conotoxin peptides generally have a core sequence termed the κ7/2/1/3 core and is represented as Cys-Cys-Xaa-Xaa-Xaa-Xaa-Xaa- Xaa-Cys-Xaa-Xaa-Cys-Xaa-Cys-Xaa-Xaa-Xaa-Cys (SEQ ID NO:3).

11 Claims, No Drawings

CONOTOXIN PEPTIDES

CROSS REFERENCE TO RELATED APPLICATION

This application is a continuation-in-part of application Ser. No. 08/137,800, filed Oct. 19, 1993, now U.S. Pat. No. 5,514,774, which in turn is a continuation-in-part of application Ser. No. 08/084,848, filed Jun. 29, 1993, now U.S. Pat. No. 5,432,155 both of which are incorporated herein by reference.

This invention was made with Government support under Grant No. GM-22737 awarded by the National Institutes of Health, Bethesda, Md. The United States Government has certain rights in the invention.

BACKGROUND OF THE INVENTION

This invention relates to relatively short peptides, and more particularly to peptides between about 10 and about 45 residues in length, which are naturally available in minute amounts in the venom of the cone snail or analogous to the naturally available peptides, and which include two or three cyclizing disulfide linkages. The peptides disclosed herein belong to a related family, the "A-lineage" conotoxin peptides.

The publications and other materials used herein to illuminate the background of the invention, and in particular, cases to provide additional details respecting the practice, are incorporated by reference, and for convenience are numerically referenced in the following text and respectively grouped in the appended bibliography.

Mollusks of the genus Conus produce a highly toxic venom which enables them to carry out their unique predatory lifestyle. Prey are immobilized by the venom which is injected by means of a highly specialized venom apparatus, a disposable hollow tooth which functions both in the manner of a harpoon and a hypodermic needle.

Few interactions between organisms are more striking than those between a venomous animal and its envenomated victim. Venom may be used as a primary weapon to capture prey or as a defense mechanism. These venoms disrupt essential organ systems in the envenomated animal, and many of these venoms contain molecules directed to receptors and ion channels of neuromuscular systems.

Predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

Cone snails that produce these toxic peptides, which are generally referred to as conotoxins or conotoxin peptides, are a large genus of venomous gastropods comprising approximately 500 species. All cone snail species are predators that inject venom to capture prey, and the spectrum of animals that the genus as a whole can envenomate is broad. A wide variety of hunting strategies are used; however, every Conus species uses fundamentally the same basic pattern of envenomation.

The major paralytic peptides in these fish-hunting cone venoms were the first to be identified and characterized. In *C. geographus* venom, three classes of disulfide-rich peptides were found: the α-conotoxin peptides (which target and block the nicotinic acetylcholine receptors); the μ-conotoxin peptides (which target and block the skeletal muscle $Na^+$ channels); and the ω-conotoxin peptides (which target and block the presynaptic neuronal $Ca^{2+}$ channels). However, there are multiple homologs in each toxin class; for example, there are at least five different ω-conotoxin peptides present in *C. geographus* venom alone. Considerable variation in sequence is evident, and when different ω-conotoxin peptide sequences were first compared, only the cysteine residues that are involved in disulfide bonding and one glycine residue were found to be invariant. Another class of conotoxins found in *C. geographus* venom is that referred to as conantokins, which cause sleep in young mice and hyperactivity in older mice and are targeted to the NMDA receptor. Each cone venom appears to have its own distinctive group, or signature, of different conotoxin sequences.

Many of these peptides have now become fairly standard research tools in neuroscience. μ-Conotoxin peptides, because of their ability to preferentially block muscle but not axonal $Na^+$ channels, are convenient tools for immobilizing skeletal muscle without affecting axonal or synaptic events. ω-Conotoxin peptides have become standard pharmacological reagents for investigating voltage-sensitive $Ca^{2+}$ channels and are used to block presynaptic termini and neurotransmitter release. The α-conotoxins have various clinical uses. One such use is their utility as clinical muscle relaxants because of their ability to achieve antagonistic blockage of the mammalian neuromuscular junction nAChRs. Another use for the α-conotoxins is in the diagnosis of myasthenia gravis (33, 34).

Some α-conotoxins have been found to bind preferentially to neuronal nicotinic receptors rather than to neuromuscular receptors. Such neuronal receptors are found on small-cell lung carcinomas (SCLCs). These α-conotoxins bind to the neuronal receptors and inhibit the proliferation of small-cell lung carcinomas which is caused by nicotine or cytosine stimulation.

Additional conotoxin peptides having the different general properties described above continue to be sought.

SUMMARY OF THE INVENTION

The present invention is directed to A-lineage conotoxin peptides. The A-lineage conotoxin peptides are conotoxin peptides that have strong homology in the signal sequence and the 3'-untranslated region of the genes coding for these peptides to the sequences in the α-conotoxin peptides. The A-lineage conotoxin peptides can be identified by performing polymerase chain reaction (PCR) amplification of Conus cDNA libraries or cDNA prepared by reverse transcription of venom duct mRNA, using primers based on the signal sequence and the 3'-untranslated region. The A-lineage conotoxin peptides include the α-conotoxin peptides, the α-conotoxin-like peptides and the κ-conotoxin peptides, described further below.

The α-conotoxin peptides generally share a "core" sequence motif. This core sequence is termed the α3/5 core, which is represented as Cys-Cys-Xaa-Xaa-Xaa-Cys-Xaa-Xaa-Xaa-Xaa-Cys (SEQ ID NO:1). This core sequence can be further defined wherein the initial group of amino acids is $Xaa_1$-Pro-Ala, where $Xaa_1$ is Asn or His. The α-conotoxin-like peptides generally share a core sequence termed the α4/7 core, which is represented as Cys-Cys-Xaa-Xaa-Xaa-Xaa-Cys-Xaa- Xaa-Xaa-Xaa-Xaa-Xaa-Xaa-Cys (SEQ ID NO:2). The κ-conotoxin peptides generally have a core sequence termed the κ7/2/1/3 core, which is represented as Cys-Cys-Xaa-Xaa-Xaa-Xaa-Xaa-Xaa- Xaa-Cys-Xaa-Xaa-Cys-Xaa-Cys-Xaa-Xaa-Xaa-Cys (SEQ ID NO:3). Despite these common core sequences, there may be some variations in some members of each group as described further below. For example, U002 has a core sequence of α4/3.

The peptide groups within the A-lineage conotoxin peptides have diverse pharmacological activity. The α-conotoxin peptides are potent inhibitors of synaptic transmission at the neuromuscular junction. These peptides are generally nicotinic acetylcholine receptor blockers. The κ-conotoxin peptides have activities against voltage-sensitive potassium or sodium channels.

DETAILED DESCRIPTION OF THE PREFERRED EMBODIMENTS

Fish-hunting cone snails use a variety of paralytic peptides for envenomating their prey. The first Conus peptide isolated and characterized was a 13-amino-acid basic peptide from the venom of Conus geographus, α-conotoxin GI, which inhibits the nicotinic acetylcholine receptor at the neuromuscular junction of vertebrates. α-Conotoxins are used by a number of fish-hunting Conus species to block the neuromuscular junction of their prey. Six α-conotoxins from three different fish-hunting Conus species have been biochemically characterized.

All α-conotoxins purified from Conus venoms to date (shown in Table I) have several common structural features; there are 12 "core" amino acids that define the minimal functional unit for a high affinity α-conotoxin; the consensus sequence from the six different α-conotoxins is indicated in the Table. The most unusual α-conotoxin is α-conotoxin SII from Conus striatus, in which an additional disulfide bond is present. However, within the core sequence of all α-conotoxins, two disulfide bonds and a number of other amino acids are highly conserved.

TABLE I

α-Conotoxin Peptides

| Peptide | Sequence | SEQ ID NO: |
|---|---|---|
| GI | ECCNPACGRHYSC* | 4 |
| GIA | ECCNPACGRHYSCGK | 5 |
| GII | ECCHPACGKHFSC* | 6 |
| MI | GRCCHPACGKNYSC* | 7 |
| SI | ICCNPACGPKYSC* | 8 |
| SIA | YCCHPACGKNFDC* | 9 |
| SII | GCCCNPACGPNYGCGTSCS | 10 |
| Consensus | N F | |
| Core Sequence | CCHPACGXXYXC | 11 |

*C-terminus is amidated.

Recently, predicted precursor structures for α-conotoxins from C. geographus were determined by a sequence analysis of cDNA clones encoding α-conotoxin GI and its homologs. The precursor of GI is a prepropeptide of 64 amino acids. For Conus peptides in general, the signal sequence and the 3' untranslated region adjacent the open reading frame are highly conserved. PCR primers were made using these α-conotoxin GI sequences, with the aim of deducing the sequences of additional α-conotoxin homologs from other Conus venoms. The strategy was to start with either messenger RNA or a cDNA library from a particular Conus venom duct, and to selectively amplify sequences related to the α-conotoxins.

The results of this PCR strategy are described in further detail below. As will be demonstrated, a remarkable variety of peptides appear to have very close kinship to the α-conotoxins. It was expected that only a small set of peptides closely related to α-conotoxin GI would be identified. However, a larger evolutionary grouping, termed a Conus peptide lineage (specifically the A-lineage conotoxin peptides) was uncovered. The lineage which includes the α-conotoxin peptides comprises a rich structural and pharmacological diversity of Conus peptides. Furthermore, it appears that this lineage was well-established early in the evolution of Conus, and peptides belonging to the lineage may well be found in the venoms of all Conus species. However, most of these peptides differ significantly, to a lesser or greater degree, from the consensus sequence deduced for the α-conotoxin peptides in Table I.

The present invention is directed to A-lineage conotoxin peptides. The A-lineage conotoxin peptides are conotoxin peptides that have strong homology in the signal sequence and the 3'-untranslated region of the genes coding for these peptides to the sequences in the α-conotoxin peptides. The A-lineage conotoxin peptides can be identified by performing polymerase chain reaction (PCR) amplification of Conus cDNA libraries or eDNA prepared by reverse transcription of venom duct mRNA, using primers based on the signal sequence and the 3' untranslated region. The A-lineage conotoxin peptides include the α-conotoxin peptides, the α-conotoxin-like peptides and the κ-conotoxin peptides, described further below.

The α-conotoxin-peptides generally share a "core" sequence motif. This core sequence is termed the α3/5 core, which is represented as Cys-Cys-Xaa-Xaa-Xaa-Cys-Xaa-Xaa-Xaa-Xaa-Xaa-Cys (SEQ ID NO:1). This core sequence can be further defined wherein the initial group of amino acids is Xaa$_1$-Pro-Ala, where Xaa$_1$ is Asn or His. The α-conotoxin-like peptides generally share a core sequence termed the α4/7 core, which is represented as Cys-Cys-Xaa-Xaa-Xaa-Xaa-Cys-Xaa- Xaa-Xaa-Xaa-Xaa-Xaa-Xaa-Cys (SEQ ID NO:2). The κ-conotoxin peptides generally have a core sequence termed the κ7/2/1/3 core, which is represented as Cys-Cys-Xaa-Xaa-Xaa-Xaa-Xaa-Xaa- Xaa-Cys-Xaa-Xaa-Cys-Xaa-Cys-Xaa-Xaa-Xaa-Cys (SEQ ID NO:3). Despite these common core sequences, there may be some variations in some members of each group as described further below. For example, U002 has a core sequence of α4/3.

The peptide groups within the A-lineage conotoxin peptides have diverse pharmacological activity. The α-conotoxin peptides are potent inhibitors of synaptic transmission at the neuromuscular junction. These peptides are generally nicotinic acetylcholine receptor blockers. The κ-conotoxin peptides have activities against voltage-sensitive potassium or sodium channels.

More specifically, the present invention is directed to the following A-lineage conotoxin peptides:

SII: Gly-Cys-Cys-Cys-Asn-Pro-Ala-Cys-Gly-Pro-Asn-Tyr-Gly-Cys-Gly-Thr-Ser-Cys-Ser-Xaa$_1$(SEQ ID NO:10). Xaa$_1$ may be des-Xaa$_1$ or Arg-Thr-Leu.

U002: Gly-Cys-Cys-Ser-Asp-Pro-Arg-Cys-Ala-Trp-Arg-Cys (SEQ ID NO:12). The C-terminus is preferably amidated.

CE-1: Arg-Asp-Xaa$_1$-Cys-Cys-Tyr-His-Pro-Thr-Cys-Asn-Met-Ser-Asn-Pro-Gln-Ile-Cys (SEQ ID NO:13). Xaa$_1$ may be Pro or preferably hydroxy-Pro, and the C-terminus is preferably amidated.

BN-1: Gly-Cys-Cys-Ser-His-Xaa$_1$-Ala-Cys-Ser-Val-Asn-Asn-Xaa$_2$-Xaa$_3$-Ile-Cys (SEQ ID NO:14). Xaa$_1$ or Xaa$_2$ may be Pro or hydroxy-Pro, and Xaa₃ may be Asp or β-carboxyaspartate. The C-terminus is preferably amidated.

BN-2: Glu-Cys-Cys-Thr-His-Xaa₁-Ala-Cys-His-Val-Ser-His-Xaa₂-Glu-Leu-Cys (SEQ ID NO:15). Xaa₁ or Xaa₂ may be Pro or hydroxy-Pro. The C-terminus is preferably amidated.

BN-3: Asp-Tyr-Cys-Cys-His-Arg-Gly-Pro-Cys-Met-Val-Trp-Cys (SEQ ID NO:16). The C-terminus is preferably amidated.

CR-1: Gln-Asn-Cys-Cys-Ser-Ile-Pro-Ser-Cys-Trp-Glu-Lys-Tyr-Lys-Cys-Xaa₁ (SEQ ID NO:17). Xaa₁ may be Ser or Asn.

CR-2: Gly-Cys-Cys-Ala-Ile-Arg-Glu-Cys-Arg-Leu-Gln-Asn-Ala-Ala-Tyr-Cys-Gly-Gly-Ile-Tyr (SEQ ID NO:18).

MG-1: Gly-Cys-Cys-Ser-Asn-Xaa₁-Val-Cys-His-Leu-Glu-His-Ser-Asn-Leu-Cys (SEQ ID NO:19). Xaa₁ may be Pro or hydroxy-Pro, and the C-terminus is preferably amidated.

SL-1: Gly-Gly-Cys-Cys-Ser-Phe-Xaa₁-Ala-Cys-Arg-Lys-Tyr-Arg-Xaa₂-Xaa₃-Met-Cys-Gly (SEQ ID NO:20). Xaa₁ or Xaa₂ may be Pro or hydroxy-Pro, and Xaa₃ may be Glu or γ-carboxyglutamate. The C-terminus is preferably amidated.

SL-2: Ala-Cys-Cys-Ser-Tyr-Xaa₁-Pro-Cys-Asn-Val-Asn-Tyr-Xaa₂-Xaa₃-Ile-Cys-Gly-Gly-Arg (SEQ ID NO:21). Xaa₁ or Xaa₂ may be Pro or hydroxy-Pro, and Xaa₃ may be Glu or γ-carboxyglutamate. The C-terminus is preferably amidated.

ST-1: Asn-Gly-Cys-Cys-Arg-Asn-Pro-Ala-Cys-Glu-Ser-His-Arg-Cys-Gly (SEQ ID NO:22).

OC-1: Asn-Val-Val-Thr-Ser-Phe-Glu-Pro-Thr-Thr-Leu-Ala-Pro-Val-Pro-Ser-Asp- Cys-Cys-Gln-Val-Ser-Ser-Cys-Trp-Asn-Leu-Tyr-Gly-Leu-Glu-Cys-Thr-Gly-Ile-Thr-Arg-Arg-Arg- Thr-Leu (SEQ ID NO:23).

OC-2: Asn-Val-Ala-Ile-Thr-Ser-Phe-Glu-Pro-Thr-Thr-Leu-Ala-Pro-Val-Pro-Ser-Asp-Cys- Cys-Gln-Val-Ser-Ser-Cys-Trp-Asn-Leu-Tyr-Gly-Pro-Glu-Cys-Thr-Gly-Ile-Thr-Arg-Arg-Arg-Thr- Leu (SEQ ID NO:24).

SVIIIA: Gln-Lys-Glu-Leu-Val-Pro-Ser-Val-Ile-Thr-Thr-Cys-Cys-Gly-Tyr-Asp-Pro-Gly- Thr-Met-Cys-Pro-Pro-Cys-Arg-Cys-Thr-Asn-Ser-Cys-Pro-Thr-Lys-Pro-Lys-Lys-Pro-Xaa₁ (SEQ ID NO:25). Xaa₁ is des-Xaa₁ or Gly-Arg-Arg-Asn-Asp (SEQ ID NO:26). When Xaa₁ is des-Xaa₁, the C-terminus is preferably amidated.

MVIII: Ala-Pro-Xaa₁-Leu-Val-Val-Thr-Ala-Thr-Thr-Asn-Cys-Cys-Gly-Tyr-Asn-Pro-Met- Thr-Ile-Cys-Pro-Pro-Cys-Met-Cys-Thr-Tyr-Ser-Cys-Pro-Pro-Lys-Arg-Lys-Pro-Xaa₂ (SEQ ID NO:27). Xaa₁ is Glu or γ-carboxyglutamate, and Xaa₂ is des-Xaa₂ or Gly-Arg-Arg-Asn-Asp (SEQ ID NO:26). When Xaa₂ is des-Xaa₂, the C-terminus is preferably amidated.

SM-1: Glx-Thr-Trp-Leu-Val-Pro-Ser-Thr-Ile-Thr-Thr-Cys-Cys-Gly-Tyr-Asp-Pro-Gly- Thr-Met-Cys-Pro-Thr-Cys-Met-Cys-Asp-Asn-Thr-Cys-Lys-Pro-Lys-Pro-Lys-Lys-Ser-Xaa₁ (SEQ ID NO:28). Xaa₁ is des-Xaa₁ or Gly-Arg-Arg-Asn-Asp (SEQ ID NO:26). When Xaa₁ is des-Xaa₁, the C-terminus is preferably amidated.

SM-2: Ala-Pro-Trp-Leu-Val-Pro-Ser-Thr-Ile-Thr-Thr-Cys-Cys-Gly-Tyr-Asp-Pro-Gly-Ser- Met-Cys-Pro-Pro-Cys-Met-Cys-Asn-Asn-Thr-Cys-Lys-Pro-Lys-Pro-Lys-Lys-Ser-Xaa₁ (SEQ ID NO:29). Xaa₁ is des-Xaa₁ or Gly-Arg-Arg-Asn-His (SEQ ID NO:30). When Xaa₁ is des-Xaa₁, the C-terminus is preferably amidated.

U007: Arg-Asp-Xaa₁-Cys-Cys-Tyr-His-Pro-Thr-Cys-Asn-Met-Ser-Asn-Pro-Gln-Ile-Cys (SEQ ID NO:31). Xaa₁ is Pro or hydroxy-Pro. The C-terminus is preferably amidated.

U008: Arg-Asp-Xaa₁-Cys-Cys-Ser-Asn-Pro-Ala-Cys-Asn-Val-Asn-Asn-Pro-Gln-Ile-Cys (SEQ ID NO:32). Xaa₁ is Pro or hydroxy-Pro. The C-terminus is preferably amidated.

U011: Gly-Cys-Cys-Gly-Pro-Tyr-Xaa₁-Asn-Ala-Ala-Cys-His-Xaa₂-Cys-Gly-Cys-Lys- Val-Gly-Arg-Xaa₃-Xaa₄-Tyr-Cys-Asp-Arg-Xaa₅-Ser-Gly-Gly (SEQ ID NO:33). Xaa₁, Xaa₂, Xaa₃, Xaa₄ and Xaa₅ are Pro or preferably hydroxy-Pro.

MII: Gly-Cys-Cys-Ser-Asn-Pro-Val-Cys-His-Leu-Glu-His-Ser-Asn-Leu-Cys (SEQ ID NO:54). The C-terminus is preferably amidated.

Conotoxin peptides purified from Conus species generally contain hydroxy-Pro in place of Pro at many of the prolyl residues. Conotoxin peptides synthesized with either Pro or hydroxy-Pro have the biological activities described herein. Thus, Pro or hydroxy-Pro may be used at any prolyl or hydroxy-prolyl residues of the peptides identified herein, and they are considered to be equivalents. Thus, for example, κ-conotoxin peptides, such as SVIIIA, MVIII, Sm-1 or Sm-2, preferably contain all hydroxy-Pro residues. In addition to the post-translational processing of conotoxin peptides to modify prolyl residues to hydroxy-Pro, other residues are also post-translationally modified in the snail. These residues include Glx or Asx, which may be modified to γ-carboxyglutamate or β-carboxyaspartate, respectively. Such modification is seen when the residue is at the N-terminus of the conotoxin peptide. One example of this modification is found in MVIII where Xaa₁ at position 3 is preferably γ-carboxyglutamate. Additional post-translational modification may involve the glycosylation of Ser and/or Thr residues, especially in the κ-conotoxin peptides at positions 7 and/or 8 of the mature peptide. Accordingly, conotoxin peptides having these modifications are considered to be equivalents of the sequences specified above and within the scope of the present invention.

The elucidation of the prepropeptide structure of two Conus geograrphus α-conotoxin peptides provided the opportunity for identifying other peptides with significant homology in their messenger RNA sequences. A PCR approach, which requires both signal sequence homology, as well as homology in the 3' untranslated region to the α-conotoxin peptides, has revealed a structurally and pharmacologically diverse group of peptides which apparently share very close evolutionary kinship. This group comprises not only the tightly-defined family of α-conotoxin peptides as originally understood, but mature peptides that might seem totally unrelated structurally and pharmacologically to the α-conotoxin peptides. As described above, this entire group of conotoxin peptides with strong homologies in their precursor and messenger RNA sequences has been named the "A-lineage" (after α-conotoxin peptides, the first family of peptides discovered in the lineage) comprising several structural classes and pharmacological families of Conus peptides.

The PCR primers used to identify Conus peptides related to α-conotoxin peptides were based on the sequence of a cDNA clone encoding α-conotoxin peptide GI from *C. geographus* venom. As shown in Table I, α-conotoxin peptides have also been isolated from *C. striatus* and *C. magus*. To ascertain that the primers would identify bona fide α-conotoxin peptide clones from other Conus species, the PCR amplification technology described above was first applied to these two fish-hunting species, with well characterized α-conotoxin peptides. The sequences of mature peptides deduced from these analyses are shown in Table II.

As expected, cDNA clones of α-conotoxin peptides which had been characterized by a conventional biochemical approach were identified from the PCR amplification of a cDNA library from *C. striatus*. The predicted precursor sequences of α-conotoxin peptides SI and SII are virtually identical in the first 42 amino acids of the prepro regions of the precursors to the corresponding sequence of the α-conotoxin peptide GI precursor (93% identity). The relevant sequences are compared in Table III.

first stage of immobilization observed upon *C. striatus* envenomation. However, there were a number of minor sequence differences: Ser-3 in κ-conotoxin peptide SVIII is replaced by Glu in SVIIIA. More strikingly, the C-terminal Cys residue of κ-conotoxin peptide SVIII is extended in κ-conotoxin peptide SVIIIA by 12 more amino acids.

In an attempt to resolve these differences, direct amplification of mRNA from *C. striatus* venom ducts was carried out. The original cDNA library was made using specimens

TABLE II

Predicted Mature Conotoxin Sequences from *C. striatus* and *C. magus*

| Peptide | Sequence | SEQ ID NO | 1st PCR | 2nd PCR |
|---|---|---|---|---|
| *Conus striatus* | | | | |
| SI | EICCNPACGPKYSC* | 34 | $2^1$ | $2^1$ |
|  |  |  | $1^2$ | $0^2$ |
| SII | GCCCNPACGPNYGCGTSCSRTL | 55 | $5^1$ | $3^1$ |
|  |  |  | $4^2$ | $0^2$ |
| ST-1 | NGCCRNPACESHRCG | 22 | $1^2$ | $0^2$ |
| SVIII | QKSLVPSVITTCCGYDPGTMCPPCRCTNSC* | 35 | $2^2$ | $0^2$ |
| SVIIIA | QKELVPSVITTCCGYDPGTMCPPCRCTNSCPTKPKK<u>PG</u>RRND$^3$ | 56 | $2^1$ | $1^1$ |
| *Conus magus* | | | | |
| MG-1 | GCCSNPVCHLEHSNLC* | 19 | 1 | 1 |
| MVIII | APELVVTATTNCCGYNPMTICPPCMCTYSCPPKRK<u>PG</u>RRND$^3$ | 57 | 3 | 6 |

*C-terminus is amidated.
$^1$Hawaii
$^2$Phillipines
$^3$Cleavage is expected between the underlined amino acid residues.

TABLE III

Prepropeptide Sequences of α-Conotoxin Peptides

| Peptide NO | Sequence | SEQ ID |
|---|---|---|
| GI | MGMRMMFTVFLLVVLATTVVSFPSERASDGRDDTAKDEGSDM-EKLVEKKE-CCNPACGRHYSCGR----- | 36 |
| SIB | MGMRMMFTVFLLVVLATTVVSFPSDRASDGRDDEAKDERSDMHESD--RKEICCNPACGPKYSCGR----- | 37 |
| SIIA | MGMRMMFTVFLLVVLATTVVSFPSDRASDGRDDEAKDERSDMHESDRNGRGCCCNPACGPNYGCGTSCSRTL | 38 |

However, the PCR amplification of *C. striatus* venom yielded two clearly resolved bands that could readily be separated by gel electrophoresis. From the faster-moving band, a total of 12 clones were sequenced from two independent PCR amplifications; eight of these proved to be the precursors for α-conotoxin peptide SII, and four encoded α-conotoxin peptide SI. The mature toxin predicted by the cDNA clone has an extra glutamate residue at the N-terminus of α-conotoxin peptide SI; otherwise, the sequences are identical. Either there is unexpected further processing of the peptide encoded in mRNA to the mature form, or the cloned sequence is a polymorphic variant of α-conotoxin peptide SI.

The higher molecular weight PCR amplification product was also cloned, and three independent clones were analyzed. These all encoded the peptide labeled κ-conotoxin peptide SVIIIA which is considerably longer than the predicted mature peptide sequence of α-conotoxin peptides SI or SII. Furthermore, SVIIA is almost identical in sequence to a peptide recently characterized from *C. striatus* venom, κ-conotoxin peptide SVIII, an excitotoxin important for the of *C. striatus* that came from Hawaii, while the PCR amplification of venom duct mRNA was carried out using specimens from the Philippines (also the source of the venom from which κ-conotoxin peptide SVIII was purified). Six clones from the faster-moving PCR amplification band from mRNA were analyzed; four were α-conotoxin peptide SII and one encoded α-conotoxin peptide SI. However, the sixth clone encoded a new peptide, ST-1, the predicted sequence of which is shown in Table II.

The more slowly-moving PCR band gave a clone which encodes a predicted prepropeptide that corresponds exactly to κ-conotoxin peptide SVIII.

Thus, from *C. striatus* alone, five different Conus peptides were obtained by analyzing clones made from the PCR amplification using α-conotoxin peptide sequences. Recovery of only two of these, α-conotoxin peptides SI and SII, were predicted. Also found was MG-1, a peptide generally similar in structure to the α-conotoxin peptides, but never previously characterized, and two known peptide sequences belonging to an entirely unrelated family, the κ-conotoxin peptides. The results also suggest that there is polymorphism in κ-conotoxin peptide sequences between Hawaiian and Philippine forms, with one amino acid substitution and a long C-terminal tail being present in Hawaiian but not Philippine specimens. Thus, the diversity of the peptides related to the α-conotoxin peptide family picked up by PCR in *C. striatus* has proven to be unexpectedly complex.

A more limited analysis of PCR products from *C. magus* was also carried out. Eleven clones were sequenced from two independent amplifications; all clones fell in one of two classes. The most abundant class (nine out of 11 clones) gave a predicted sequence that was essentially identical to κ-conotoxin peptide MVIII, as shown in Table II. In addition, a peptide more closely related structurally to α-conotoxin peptides was also recovered. A clone which encoded α-conotoxin peptide MI, the α-conotoxin peptide from *C. magus* venom, was not recovered.

One complication that emerged when the cDNA sequence and the actual sequence of purified κ-conotoxin peptide MVIII were compared, was the discovery that the last five amino acids are excised to give an amidated C-terminus. It is noteworthy that the C-terminal sequence would not normally be predicted to be subject to proteolytic cleavage. The probable true C-terminus of κ-conotoxin peptides MVIII and SVIIIA are indicated by an arrow in Table II.

The venoms of both *C. magus* and *C. striatus* proved to have κ-conotoxin peptide precursors as a significant fraction of all clones obtained using the α-conotoxin precursor sequences. Since κ-conotoxin peptides are believed to be important components for those fish-hunting cone snails ("harpooners") that harpoon their prey before engulfing it, it was desired to examine other Conus species believed to be fish-hunting, but which have never been observed to harpoon their prey. Two little-known Conus species that are believed to be piscivorous are *C. ochroleucus* and *C. sulcatus*. A PCR amplification was done from mRNA of *C. ochroleucus*, and a cDNA library of *C. sulcatus*.

The results are shown in Table IV. Nineteen clones from *C. sulcatus* and nine clones from *C. ochroleucus* were sequenced from two independent amplifications. In *C. sulcatus*, the same sequence (SL-1) accounted for 18/19 clones, and a closely related peptide (SL-2) was the only other one identified. In contrast, the *C. ochroleucus* clones encoded two peptides (OC-1 and OC-2) that were considerably longer and homologous to each other.

TABLE IV

Predicted Mature Conotoxin Sequences from
*C. sulcatus*, *C. orchroleucus* and *C. stercusmuscarum*

| Peptide | Sequence | SEQ ID NO | No. of Clones Analyzed | |
| --- | --- | --- | --- | --- |
| | | | 1st PCR | 2nd PCR |
| *Conus sulcatus* | | | | |
| SL-1 | GGCCSFPACRKYRPEMCG* | 20 | 12 | 6 |
| SL-2 | ACCSYPPCNVNYPEICGGR* | 21 | 0 | 1 |
| *Conus ochroleucus* | | | | |
| OC-1 | NVVVTSFEPTTLAPVPSDCCQVSSCWNLYGLECTGITRRRTL | 23 | 3 | 4 |
| OC-2 | NVAITSFEPTTLAPVPSDCCQVSSCWNLYGPECTGITRRRTL | 24 | 1 | 1 |
| *Conus stercusmuscarum* | | | | |
| SM-1 | ZTWLVPSTITTCCGYDPGTMCPTCMCDNTCKPKPKKSGRRND | 58 | 2 | 2 |
| SM-2 | APWLVPSTITTCCGYDPGSMCPPCMCNNTCKPKPKKSGRRNH | 59 | 1 | 2 |

*C-terminus is amidated.

Although the predicted mature toxins from *C. sulcatus* and *C. ochroleucus* are very different in length (19–20 amino acids for *C. sulcatus* and 42 amino acids for *C. ochroleucus*), the peptides nevertheless show the same spacing in their core sequences. From the first Cys residue to the last, all of the peptides have the core motif CC4C7C. This same motif was also found in MG-1, the α-conotoxin-like peptide from *C. magus* shown in Table II. The *C. ochroleucus* peptides are much longer mainly because they have an extended N-terminal and C-terminal tail, compared to the *C. sulcatus* and *C. magus* peptides. It is noteworthy that no κ-conotoxin peptides were uncovered in these species.

A third fish-hunting Conus species, known to be a harpooner, was also analyzed. *C. stercusmuscarum* is a species from which no α-conotoxin peptides have been isolated. A total of seven clones were sequenced; two predicted sequences were elucidated. By homology, it seems virtually certain that these are κ-coconotoxin peptides which have been named κ-conotoxin peptide SmVIII and κ-conotoxin peptide SmVIIIA. Thus, in *C. stercusmuscarum*, a harpooner like *C. striatus* and *C. magus*, the κ-conotoxin peptides are identified by the PCR amplification protocol used.

The results above indicate that peptides that must be closely related evolutionarily to the α-conotoxin peptides are found in the venom ducts of all fish-hunting species examined. An investigation was made as to whether this group of peptides might also be found in non-fish-hunting species. Most of the 500 Conus species are non-piscivorous, and the two other large groups hunt gastropod mollusks, and polychaete worms. A PCR amplification from the molluscivorous Conus species, *C. bandanus* and the vermivorous species, *C. caracteristicus* was therefore carried out, and the results of an analysis of the clones from these amplifications is shown in Table V.

TABLE V

Predicted Mature Conotoxin Sequences from *C. bandanus* and *C. caracteristicus*

| Peptide | Sequence | SEQ ID NO | No. of Clones Analyzed 1st PCR | 2nd PCR |
|---|---|---|---|---|
| *Conus bandanus* | | | | |
| BN-1 | GCCSHPACSVNNPDIC* | 14 | 18 | 1 |
| BN-2 | ECCTHPACHVSHPELC* | 15 | 0 | 1 |
| BN-3 | DYCCHRGPCMVWC* | 16 | 1 | 1 |
| *Conus caracteristicus* | | | | |
| CR-1 | QNCCSIPSCWEKYKCS | 17 | 1 | 3 |
| CR-2 | GCCAIRECRLQNAAYCGGIY | 18 | 2 | 1 |

Twenty-two clones were analyzed from *C. bandanus*. Of these, 19 encoded a single peptide (BN-1), and one was found to encode a closely related sequence (BN-2). These peptides also showed the characteristic α4/7 (CC4C7C) core motif described above. The third peptide sequence (BN-3) was unrelated to the other two, and exhibited an α4/3 core sequence.

Seven clones were sequenced from *C. caracteristicus*, and were found to encode two different predicted mature peptides. Three clones encoded an α4/7 peptide (CR-1), while four out of seven encoded an α-conotoxin-like peptide (CR-2) that had an α4/5 core sequence motif. It is noteworthy that no κ-conotoxin peptide-like sequences were detected from either *C. bandanus* or *C. caracteristicus* PCR application clones.

The most surprising toxins to find as members of the A-lineage were the κ-conotoxin peptides, which have no apparent homology to the α-conotoxin peptides in amino acid sequence of the mature peptides, even the arrangement of Cys residues is entirely different. Furthermore, the κ-conotoxin peptides do not act at the acetylcholine receptor, but target either voltage-sensitive potassium or sodium channels. Thus, it was unexpected to find the very strong homology detected between α- and κ-conotoxin peptides in both signal sequence and 3' untranslated region.

A comparison of all of the prepropeptide amino acid sequences of α- and κ-conotoxin peptides is shown in Table VI. These sequences have been aligned for maximal identity. The ability of α-conotoxin peptide primers to pick up κ-conotoxin peptides is explained by the virtual identity of the two signal sequences.

TABLE VI

| Comparison of κ-Conotoxin and α-Conotoxin Prepropeptides | | |
|---|---|---|
| Peptide | Sequence | SEQ ID NO |
| SI | MGMRMMFTVFLLVVLATTVVSFPSDRASDGRDDEAKDERSDMHESD--RKEICCNPACGPKYSCGR----- | 39 |
| SVIII | MGMRMMFTVFLLVVLATNVVSTPSDRASDGRNAAVHERQKSLVPSVITT-CCGYDPGTMCPPCRCTNSCG---------- | 40 |
| SVIIIA | MGMRMMFTVFLSVVLATTVVSTPSDRASDGRNAAVHERQKELVPSVITT-CCGYDPGTMCPPCRCTNSCPTKPKKPGRRND | 41 |
| MVIII | MGMRMMFTVFLLVVLATTVVSIPSDRASDGRNAVVHERAPELVV-TATTNCCGYNPMTICPPCMCTYSCPPKRK-PGRRND | 42 |
| SmVIII | MGMRMMFTVFLLVVLATTVVSIPSDRASDGRNAAVNERQTWLVPSTITT-CCGYDPGTMCPTCMCDNTCKPKPKKSGRRND | 43 |
| SmVIIIA | MGMRMMFTVFLLVVLATTVVSIPSDRASDGRNAEVNERAPWLVPSTITT-CCGYDPGSMCPPCMCNNTCKPKPKKSGRRNH | 44 |

There is considerable homology (but not total identity) in the pro region of the precursor, and no significant identity in the mature toxin region of the prepropeptide. The putative borders between signal sequence, propeptide and mature toxin are indicated. There is no doubt that, although the mature toxins are structurally and pharmacologically unrelated to each other, the α-conotoxin peptide and κ-conotoxin peptide precursor families are in fact very closely related by evolutionary lineage.

In addition to the κ-conotoxin peptides, a variety of additional peptides more closely related to the α-conotoxin peptides, were also identified using the same PCR primers. Several of these can be aligned into a cohesive family of α-conotoxin-like peptides, which differ from the canonical α-conotoxin peptides by having different length loops between the disulfide bonds. Thus, while all α-conotoxin peptides in Table I have a typical α3/5 core (as described above), most of the additional peptides that were identified by PCR have the α4/7 core. Furthermore, if the peptides with the α4/7 motif are aligned, many have striking homology to peptides previously identified from C. obscurus and C. tulipa venoms. These sequences are shown in Table VII. In the C. obscurus and C. tulipa peptides, there is a post-translationally modified amino acid, γ-carboxyglutamate in the second loop. The α14/7 peptides predicted by the PCR methodology show great homology to these peptides, and it seems likely that the natural peptides in fact have γ-carboxyglutamate, and not glutamate, at the homologous position. There is a tantalizing suggestion that, since one of the peptides from C. bandanus has an aspartate substitution at that position, this residue may also be post-translationally modified.

peptides, are sufficiently small to be chemically synthesized. General chemical syntheses for preparing the foregoing A-lineage conotoxin peptides are described hereinafter, along with specific chemical synthesis of one of the A-lineage conotoxin peptides and indications of biological activities of these synthetic products. Various ones of these A-lineage conotoxin peptides can also be obtained by isolation and purification from specific Conus species using the techniques described in U.S. Pat. No. 4,447,356 (1) or Olivera et al. (2), the disclosures of which are incorporated herein by reference. For example, the peptides U007, U008 and U011 were obtained by purification from Conus ermineus.

Although A-lineage conotoxin peptides can be obtained by purification from the enumerated cone snails, because the amounts of A-lineage conotoxin peptides obtainable from individual snails are very small, the desired substantially pure A-lineage conotoxin peptides are best practically obtained in commercially valuable amounts by chemical synthesis. For example, the yield from a single cone snail may be about 10 micrograms or less of A-lineage conotoxin peptide. By "substantially pure" is meant that the peptide is present in the substantial absence of other biological molecules of the same type; it is preferably present in an amount of at least about 85% by weight and preferably at least about 95% of such biological molecules of the same type which are present (i.e., water, buffers and innocuous small molecules may be present). Chemical synthesis of biologically active A-lineage conotoxin peptides depends of course upon correct determination of the amino acid sequence.

The A-lineage conotoxin peptides can also be produced by recombinant DNA techniques well known in the art. Such

TABLE VII

Homology Between of α-Conotoxin and α-Conotoxin-like Peptides

| Peptide | Sequence | SEQ ID NO |
|---|---|---|
| αGI | MGMRMMFTVFLLVVLATTVVSFPSERASDGRDDTAKDEGSDM-EKLVEKK----ECCN-PACGRHYS--CGR | 45 |
| BN-1 | MGMRMMFTMFLLVVLATTVVSFASDRASD--GRNAAA--KDK-ASDLV-ALTVKGCCSHPACSVNNPDICG | 46 |
| CR-2 | MGMRMMFTVFLLVVLATTVVSFTSDRASE--GRNAAA--KDK-ASDLV-ALTVRGCCAIRECRLQNAAYCGGIY | 47 |
| MG-1 | MGMRMMFTVFLLVVLATTVVSFPSDRASD--GRNAAAN--DK-ASD-VITLALKGCCSNPVCHLEHSNLCGRRR | 48 |
| SL-1 | MGMRMMFTVFLLVVLATTVVSFNSDRDPALGGRNAAAIASDKIAS----TLRRGGCCSFPACRKYRPEMCGGRR | 49 |
| CR-1 | MGMRMMFTVFLLVVLATTVVSFTSDRASDGRNAAANA--FDLIALIAR-----QNCCSIPSCKEKYK--CS | 50 |
| BN-2 | MGMRMMFTVFLLVVLATAVLPVTLDRASDGRNAAANAKTPRLIAPFIR-----DYCCHRGPCMVW---CG | 51 |

Finally, there are other groups of peptides which belong to the A-lineage that do not belong to coherent classes. These include ST-1, BN-3 and CR-1, α-conotoxin-like peptides from C. striatus, C. bandanus and C. caracteristicus, which have core motifs other than α3/5 and α4/7. Thus, the A-lineage is quite diverse, almost certainly encompassing at least two structural classes and several pharmacological families. Furthermore, it is clearly widely-distributed in Conus venoms, since in this study A-lineage peptides from both snail-hunting and worm-hunting Conus were identified, in addition to the fish-hunting species from which the original α-conotoxin peptides were isolated.

After identification of the amino acid sequence of the conotoxin peptide, such as by purification and sequence analysis, PCR amplification, recombinant DNA techniques or the like, the mature conotoxin peptide can be synthesized using conventional techniques as described further below.

These peptides, generally termed A-lineage conotoxin techniques are described by Sambrook et al. (3) The peptides produced in this manner are isolated, reduced if necessary, and oxidized to form the correct disulfide bonds.

One method of forming disulfide bonds in the A-lineage conotoxin peptides of the present invention is the air oxidation of the linear peptides for prolonged periods under cold room temperatures. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration because the cross-linking and/or rearrangement which occurs in vivo has been found to create the biologically potent conotoxin molecule. However, because of the dilution resulting from the presence of other fractions of less biopotency, a somewhat higher dosage may be required.

A second method of forming the disulfide bonds in the A-lineage conotoxin peptides of the present invention involves the use of acetamidomethyl (Acm) as protection agent on the second and fifth cysteines during the synthesis of the A-lineage conotoxin peptides. Use of Acm on these two residues is based on the analogy with disulfide bridges in other A-lineage conotoxin peptides. The peptide with the Acm protected cysteines is air-oxidized overnight at room temperature. The bicyclic peptides are separated by HPLC and the desired isomer isolated. The final disulfide bridge is carried out by iodination. The undesired isomers are efficiently recycled by reduction to linear peptide. The desired isomer is determined by a partial reduction analysis (4). In this analysis, a sample of a bicyclic precursor is treated with tris-[2-carboxyethyl]phosphine to give linear peptide and a singly-bridged intermediate. The latter peptide is reacted with iodoacetamide, and the location of alkylated cysteine residues is established by sequence analysis.

The peptides are synthesized by a suitable method, such as by exclusively solid-phase techniques, by partial solid-phase techniques, by fragment condensation or by classical solution couplings. The employment of recently developed recombinant DNA techniques may be used to prepare these peptides, particularly the longer ones containing only natural amino acid residues which do not require post-translational processing steps.

In conventional solution phase peptide synthesis, the peptide chain can be prepared by a series of coupling reactions in which the constituent amino acids are added to the growing peptide chain in the desired sequence. The use of various N-protecting groups, e.g., dicyclohexylcarbodiimide or carbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organisthen Chemie (Houben-Weyl): Synthese von Peptiden," (5). Techniques of exclusively solid-phase synthesis are set forth in the textbook, "Solid-Phase Peptide Synthesis," (6), and are exemplified by the disclosure of U.S. Pat. No. 4,105,603 (7). The fragment condensation method of synthesis is exemplified in U.S. Pat. No. 3,972,859 (8). Other available syntheses are exemplified by U.S. Pat. Nos. 3,842,067 (9) and 3,862,925 (10).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (11). Choro-methylated resins are commercially available from Bio Rad Laboratories (Richmond, Calif.) and from Lab. Systems, Inc. The preparation of such a resin is described by Stewart et al. (6). BHA and MBHA resin supports are commercially available, and are generally used when the desired polypeptide being synthesized has an unsubstituted amide at the C-terminus. Thus, solid resin supports may be any of those known in the art, such as one having the formulae —O—$CH_2$-resin support, —NH BHA resin support, or —NH—MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (12) can be used, or should still other groups than the free acid be desired at the C-terminus, it may be preferable to synthesize the peptide using classical methods as set forth in the Houben-Weyl text (5).

The C-terminal amino acid, protected by Boc and by a side-chain protecting group, if appropriate, can be first coupled to a chloromethylated resin according to the procedure set forth in K. Horiki et al. (13), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (14).

After removal of the α-amino-protecting group, the remaining α-amino- and side chain-protected amino acids are coupled step-wise in the desired order to obtain the intermediate compound defined hereinbefore, or as an alter-native to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (14) and Kapoor (15).

Each protected amino acid or amino acid sequence is introduced into the solid-phase reactor in about a twofold or more excess, and the coupling may be carried out in a medium of dimethylformamide (DMF): $CH_2Cl_2$ (1:1) or in DMF or $CH_2Cl_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (16). Coupling reactions can be performed automatically, as on a Beckman 990 automatic synthesizer, using a program such as that reported in Rivier et al. (17).

After the desired amino acid sequence has been completed, the intermediate peptide can be removed from the resin support by treatment with a reagent, such as liquid hydrogen fluoride, which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptidoresin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF), followed by oxidation as described above.

The examples below describe the chemical synthesis of SII. The conotoxin peptides disclosed herein are similarly synthesized using the conventional techniques described above.

EXAMPLES

The present invention is described by reference to the following Examples, which are offered by way of illustration and are not intended to limit the invention in any manner. Standard techniques well known in the art or the techniques specifically described below were utilized.

EXAMPLE 1

Purification and Analysis of α-Conotoxin SII

Purification of Conotoxins from *C. striatus* Venom

Purification of the peptides from *C. striatus* venom involved initial size fractionation of its components by chromatography on Sephadex G-25 as previously described (18), followed by HPLC on semipreparative reverse-phase $C_{18}$ columns (Ultropac TSK ODS-120T, 7.8×300 mm, 10 mm; or VYDAC $C_{18}$, 10×250 mm, 5 mm; a gradient of acetonitrile in 0.1% TFA was used). Isolation of peptides from selected peaks usually required one or two more runs on analytical reverse-phase $C_{18}$ columns. Gradients of acetonitrile in 0.1% TFA were used to elute the peptides.

Sequence Analysis of Conotoxins

Peptide SII was reduced and carboxymethylated, and then analyzed in a spinning-cup sequencer as described previously (19).

Purification and Characterization of α-Conotoxin Peptide SII

In the course of purification of a-conotoxin peptides SI and SIA, additional fractions which cause paralysis in fish were identified. One of these activities eluted closely to SI and SIA. The paralytic fraction was purified to >90% homogeneity, and its amino acid composition was determined. An amino acid sequencing nm gave results consistent with a 19 amino acid peptide with the sequence indicated in Table I. The sequence assignments in Table I match the determined amino acid composition. Further confirmation of the sequence assignment was provided by fast atom bombardment (FAB) mass spectrometry. The FAB mass spectrometry determination yielded a MW ($MH^+$ 1790.56) which is consistent with the predicted 19 amino acid peptide with a free carboxyl terminus. Although this peptide is larger than any other α-conotoxin peptide so far characterized, it has striking homology to α-conotoxin peptide SI. This peptide has therefore been designated as α-conotoxin peptide SII. To confirm the sequence of the natural peptide, and to make more peptide available for further characterization, α-conotoxin peptide SII was synthesized.

α-Conotoxin peptide SII is generally found at lower levels in *C. striatus* venom than α-conotoxin SI, or the major ω-conotoxin, SVIA. However, there is considerable variation in the levels of the toxins from one venom sample to the next. Although the levels of SI and SII have been found to be approximately equal in one venom sample, more typically α-conotoxin peptide SII is found to be ca. 20% of a-conotoxin peptide SI and ca. 10% of ω-conotoxin peptide SVIA.

EXAMPLE 2

Synthesis of α-Conotoxin SII

Synthesis of α-Conotoxin SII

Synthesis was carried out by the solid-phase procedure of Merrifield (20), following the general protocol of Gray et al. (21). Two grams of t-Boc-L-serine resin (Vega Biotechnologies Inc.; 0.60 mmol substitution/g) was used as the starting support, and Boc amino acids were purchased from Bachem. All Boc amino acids, except Boc-Gly, were of the L configuration. Side chains were protected as Cys(Mob), Ser (Bzl), Thr(Bzl). With one exception, couplings were carried out using dichloromethane as solvent and diisopropylcarbodiimide as the coupling agent. Asparagine was coupled without side-chain protection, using dimethylformamide as solvent, and 2 equiv. of hydroxybenzotriazole was added to minimize side reactions. Coupling was repeated when Pro residues made the ninhydrin test (16) an unreliable guide for completeness of reaction.

The peptide was deprotected and removed from the resin (2.0 g of peptide-resin) as the Ser C-terminal, using the low-high HF procedure of Tam et al. (22).

Extraction and Purification of Reduced SII

After completely distilling off the HF and most of the scavengers, the mixture was extracted with ~200 mL of ether/1% β-mercaptoethanol (βME). The peptide was extracted with ~200 ml of 5% HOAc/1% βME and then filtered through a 0.5 μm Millipore membrane filter to remove the precipitate that formed.

The filtrate was concentrated to ~40 mL by lyophilization and loaded onto an LH-20 column using 30% acetonitrile in 0.1% TFA as eluting buffer at a flow rate of 2.5 mL/min. Fractions were collected every three minutes for a total of 80 tubes, and those fractions that showed positive ninhydrin test were pooled and lyophilized.

Oxidation and Purification of SII

The lyophilized peptide (0.611 g) was treated with 10 mL of 6M guanidine hydrochloride/10 mM DTT, pH 9.0, and incubated at 55° C. for one hour. After cooling, the clear, yellow solution was then added dropwise to 4L of 0.05M $NH_4CO_3$, pH 8.08 (previously bubbled with $N_2$ for 1.5 hours). The reaction flask was loosely covered with paper tissue, and the mixture was allowed to air-oxidize (with magnetic stirring) at room temperature until it gave a negative Ellman's test for thiol.

The oxidized mixture was adjusted to pH 5.5 with glacial acetic acid and then filtered on a Buchner funnel (Whatman No. 1 filter paper). The filtrate was chromatographed using a $C_{18}$ RP Waters Custom Prep Pak HPLC column (Delta Pak $C_{18}$, 300-Å pore size, 15 mm) and eluted with a linear gradient of the TEAP system, pH 6.0 (23), at a flow rate of 40 mL/min. for 50 minutes. Fractions monitored at 280 nm were collected manually every 30 seconds. The correctly folded peptide was identified by analytical HPLC using 10–20 μL of each fraction from the peaks and comparing the elution time in TFA/acetonitrile with that of the natural SII peptide. Further purification of the peptide was carried out using a semipreparative column and TFA/acetonitrile buffer system.

The peptide was synthesized by the standard methods detailed above. Starting with 2 g of Boc-Ser resin, the peptide was synthesized manually by the Merrifield procedure and was released from the resin using HF; approximately 0.6 g of reduced peptide was obtained. The peptide was oxidized by slow air oxidation at 4° C. in a large volume (4L). After five days, the oxidized peptide was purified by HPLC.

The synthetic and natural peptides have identical behavior on HPLC, and they showed similar effects on fish. Comparable paralysis and death times were observed at the three doses tested (0.5, 1.0 and 5.0 nmol/fish). Thus, by all criteria, the native and synthetic peptides are identical to each other, a direct confirmation of the sequence assignment. It is notable that although the peptide is a potent paralytic toxin to fish, no obvious effects are seen in two-week-old mice, even at 20 nmol/mouse.

EXAMPLE 3

Biological Activity of α-Conotoxin SII

Biological Assays

Injection of fish and mice was performed as previously described (18).

Synaptic responses were extracellularly recorded from cutaneous pectoris nerve-muscle preparations from Rana pipiens as previously described (24). Briefly, the lateral third of the muscle was cut away and pinned in a rectangular Sylgard trough. Synaptic responses were recorded with Pt-wire electrodes from the preparations treated with 0.2 μM α-bungarotoxin to block end-plate potentials to levels below the threshold necessary for action potential generation. Conotoxin peptides were bath-applied by replacing the bath solution with toxin-containing solution. α-Conotoxin SII reversibly blocked electrically evoked postsynaptic responses of the frog neuromuscular junction preparation.

To test whether SII affected acetylcholine receptors, the toxin's effects on spontaneous miniature end plate potentials (mepps) were measured. Spontaneous miniature end-plate potentials (mepps) were recorded intracellularly from cutaneous pectoris muscle pinned to Sylgard-coated glass cover slips and then placed in a chamber which was secured to the stage of a fluorescence microscope. Toxin was focally applied in a solution containing a tetramethylrhodamine-lysozyme conjugate (5 μM). The fluorescence of the solution allowed its location to be monitored to be sure that end-plate regions were contacted by the toxin expelled from the puffer pipet. Toxin was washed away from the end plate following withdrawal of the puffer pipet by perfusing the bath. SII (20 μM) applied from a puffer pipet reduced mepp amplitudes 45%, which recovered following washout of the toxin (n>20). This result indicates that acetylcholine receptors were reversibly blocked by the toxin.

Electrophysiological data were acquired with virtual instrument software (LabVIEW National Inst.) on Macintosh computers fitted with A/D converter hardware either from National Instruments (Lab NB) or GW Instruments (Mac-ADIOS adio).

Binding Competition Between $^{125}$I-Labeled α-Bungarotoxin and α-Conotoxin SII The results with the frog neuromuscular junction, i.e., the blockade of mini-end-plate potentials (mepps) described above, as well as the homology revealed by sequence analysis of α-conotoxin peptide SII, are strongly suggestive (but not conclusive evidence) that this peptide binds to the acetylcholine receptor at the vertebrate neuromuscular junction. In order to confirm this receptor assignment, an investigation was made as to whether α-conotoxin peptide SII bound to the ligand binding site of the nicotinic acetylcholine receptor by assaying for the ability of this peptide to compete with radiolabeled α-bungarotoxin to this site.

Binding experiments were done using a filtration assay of a post-synaptic membrane fraction isolated from electroplax of *Torpedo Califonica*. The $^{125}$I-bungarotoxin (2,000 Ci/mmol) was used at ca. $10^5$ cpm per assay; 100% binding under the condition used was 20,000 cpm. Non-specific binding, determined by preincubation with 1 μM unlabeled α-bungarotoxin, was subtracted out. The results of this experiment demonstrated that α-conotoxin peptide SII will completely displace the binding of $^{125}$I-α-bungarotoxin to the well-characterized nicotinic acetyl-choline receptor found in the Torpedo electric organ. Under the binding conditions used, the apparent $IC_{50}$ for α-conotoxin peptide SII was 8 μM; a similar analysis for the previously characterized α-conotoxin peptide SI yielded $IC_{50}$ value of 1 μM under these conditions. These data therefore directly demonstrate that α-conotoxin peptide SII interacts with the nicotinic acetylcholine receptor at the ligand binding site. Thus, both the physiological data and binding data are consistent with α-conotoxin peptide SII belonging to the α-conotoxin class which inhibits acetylcholine binding to the acetylcholine receptor at the neuromuscular junction.

EXAMPLE 4

PCR Amplification of Conotoxin Peptides

The rapid discovery of A-lineage conotoxin peptides from a variety of Conus species was made possible by the presence of highly conserved nucleic acid sequences in the cDNAs encoding this class of peptides. Specifically, it has been discovered that sequences encoding the signal sequence, pro region, 5' untranslated and 3' untranslated regions of A-lineage prepropeptides are sufficiently well conserved to provide a means of accessing these peptides by a variety of molecular techniques. A highly efficient strategy for A-lineage conotoxin peptide discovery based on the PCR amplification of A-lineage prepropeptide sequences, using PCR primers homologous to conserved portions of the α-conotoxin peptide GI cDNA, was used to identify the peptides described above in Tables II–VII. In this strategy, one PCR primer contained conserved nucleic acids encoding part of the signal sequence of the GI prepropeptide and a second PCR primer contained conserved nucleic acids from the 3' untranslated region of the GI cDNA. These two paired primers therefore target conserved nucleic acid sequences which flank the cDNA sequence encoding the class of A-lineage conotoxin peptides and support the PCR amplification of A-lineage prepropeptide encoding sequences from any suitable template of Conus venom duct cDNA.

A PCR amplification was performed on the Conus species identified in Table VIII.

Conventional PCR techniques (25, 26) were utilized with the lineage targeting oligonucleotides DHOG506 and DHOG507 to identify the peptides described in Tables II–VII. Oligonucleotide DHOB506 (5'-TCTGCGAATGGGCATGCGGATGATGTT-3') (SEQ ID NO:52) contains the first 20 base pairs encoding the α-conotoxin peptide GI signal sequence (boldfaced) as well as a seven-base-pair 5' extension to facilitate subcloning of PCR products into an appropriate DNA vector. Oligonucleotide DHOB507 (5'-TGCTCCAACGTCGTGGTTCAGAGGGTC-3') (SEQ ID NO:53) contains 20 base pairs from the 3' untranslated region of the α-conotoxin GI cDNA clone (boldfaced) as well as a seven-base-pair 5' extension to facilitate subcloning. Using oligonucleotides DHOG506 and DHOG507 as PCR primer pairs in the presence of C. bandanus venom duct cDNA gave rise to an amplification product which had an apparent size of approximately 240 base pairs in agarose gels. Subcloning and sequencing of this amplified material revealed the presence of several discrete cDNAs encoding A-lineage prepropeptides. One of these cDNAs was a clone encoding a 60 amino acid prepropeptide with the following sequence: MGMRMMFTMFLLVVLATTVVSFASDRAS-DGRNAAAKDKASDLVALTVKGCC SHPACSVNNP-DICG (SEQ ID NO:46). The C-terminal domain of this prepropeptide includes amino acids which clearly form an A-lineage conotoxin with a CC4C7C pattern. The identify of the N-terminal amino acid of the mature conotoxin is determined by the presence of a basic amino acid residue (lysine) two amino acids N-terminal to the double cystine residues. The mature toxin sequence clearly predicted from this C. bandanus cDNA therefore is GCCSHPACSVNNP-DIC* (SEQ ID NO:14; *=C-terminal amidation) which is called the C. bandanus BN-1 conotoxin peptide.

TABLE VIII

| | PCR Amplification of Conus Species | | | |
|---|---|---|---|---|
| Species | Prey | Amplified Nucleic Acid Source | # Clones Sequenced | # Types of Clones Detected |
| Conus striatus | Fish | cDNA Library mRNA | 23 | 5 |
| Conus magus | Fish | cDNA Library | 11 | 2 |
| Conus stercus-muscarum | Fish | mRNA | 7 | 2 |
| Conus ochroleucus | Fish(?) | mRNA | 9 | 2 |
| Conus sulcatus | Fish(?) | cDNA Library | 19 | 2 |
| Conus bandanus | Snails | mRNA | 22 | 3 |
| Conus caracteristicus | Worms | mRNA | 7 | 2 |

EXAMPLE 5

Biological Activity of U002

The biological activity of conotoxin peptide U002 was determined by measuring its effect on spontaneous mepps of flog cutaneous pectoris muscle and by measuring its ability to compete with α-bungarotoxin, as described above in Example 3. U002 (205 mM) was applied from a puffer pipe reduced mepp amplitudes 30%, which recovered following washout of the toxin. U002 was found to block 70% of α-bungarotoxin binding at 50 μM.

EXAMPLE 6

Biological Activity of κ-Conotoxin Peptides

A biological assay was used to determine the electrophysiological activity of κ-conotoxin peptides. In this assay, a fleshly-dissected flog neuromuscular junction preparation (cutaneous pectoris muscle) was placed in a small (approximately 30 μL) recording chamber and bathed with normal frog Ringer's solution. Electrical stimulation of the nerve results in a single action potential which was recorded extracellularly from the frog muscle. Toxin (approximately 100 nM–1 μM) was applied to the nerve-muscle preparation. The application of toxin results in repetitive action potentials in response to a single electrical stimulation of the nerve. Subsequently, the muscle begins twitching spontaneously and non-evoked (spontaneous) action potentials can be recorded. The effect of the toxin (repetitive action potentials) appears to be irreversible (effect is still present after washing the neuromuscular preparation for two hours). Addition of curare to the bath blocks the κ-toxin induced repetitive action potential indicating that a major portion (if not all) of the toxin's effect is neuronally mediated. These effects are most consistent with either potassium channel blockade or sodium channel activation.

κ-Conotoxin peptides can also be isolated using the above electrophysiological assay to screen Conus venom HPLC fractions. Active fractions are further purified until a homogeneous product is obtained.

EXAMPLE 7

Purification of α-Conotoxin MII Peptide

α-Conotoxin MII was isolated from the venom of *Conus magus* by screening for peptides which bind to neuronal nicotinic receptors of the $\alpha_3\beta_2$ subtype. Cloned DNA from rat brain encoding neuronal nicotinic receptors was used to make mRNA which was injected into Xenopus oocytes by standard techniques. This mRNA was expressed in the oocytes and the normal nicotinic receptor was made and formed part of the cell surface of the oocytes. Direct physiological effects of acetylcholine can be made on these cells. MII was found by electrophysiologically screening venom fractions against the cloned nicotinic receptors expressed in Xenopus oocytes. The assay is a standard one. The oocytes are voltage clamped and acetylcholine is added to the media containing the cells. With no toxin present the addition of acetylcholine causes a negative current which can be seen by a current tracing. The presence of a toxin will diminish or abolish this effect. Various snail venoms were tested and venom from *Conus magus* was found to be especially potent in this assay. This venom was fractionated by HPLC and the different fractions were assayed by this method. Conotoxin MII was isolated as being the active toxin. Conotoxin MII was found to antagonize the effects of acetylcholine. Thus it behaves similarly to all other α-conotoxins in the sense that it is a nicotinic acetylcholine receptor antagonist. However, MII differs from other α-conotoxins in that it potently targets the $\alpha_3\beta_2$ subtype of nicotinic receptor. It also shows potent activity at the $\alpha_7$ subtype of nicotinic receptor. α-Conotoxin MII blocks the response to acetylcholine in oocytes expressing $\alpha_3\beta_2$ nicotinic acetylcholine receptors with an $IC_{50}$ of 5–10 nM. This peptide is 2–3 orders of magnitude less active in blocking acetylcholine responses of all other tested $\alpha_x\beta_y$ nicotinic acetylcholine receptors.

EXAMPLE 8

Inhibition of SCLC Proliferation by α-Conotoxins

Small cell lung carcinoma (SCLC) cells have been found to express cholinergic nicotinic receptors (Maneckjee et al. (27); Chini et al. (28); Tarroni et al. (29); Schuller et al. (30)). These SCLC nicotinic receptors have been shown to be of neuronal type (Chini et al. (28); Tarroni et al. (29)). Nicotine and cytosine each stimulate the release of 5-hydroxytryptamine (5HT or serotonin) which acts as a potent mitogen in SCLC cells (Maneckjee et at. (27); Cattaneo et al. (31)). α-Conotoxin MI has been found to block the nicotine or cytosine induced release of serotonin and at a concentration of 1 µM it completely antagonized the nicotine and cytosine stimulation of SCLC proliferation (Codignola et al. (32)). α-Conotoxins which bind to neuronal type nicotinic receptors are suitable for preventing the proliferation of tumors such as SCLC and can be used therapeutically to inhibit such proliferation as described below. These α-conotoxins can also be used diagnostically for detecting the presence and/or location of small-cell lung tumors as described below. Although Codignola et at. (32) report that α-conotoxin MI binds to these SCLC receptors, α-conotoxin MI is not suitable for therapeutic or diagnostic use since it also binds to neuromuscular receptors and can cause paralysis which could lead to death. α-Conotoxins which do not bind to neuromuscular receptors or which have a much lower affinity for such receptors as compared to the nicotinic neuronal receptors are suitable for therapeutic or diagnostic purposes. Such peptides include the α-conotoxins MII and U002.

EXAMPLE 9

Diagnosis of SCLC Using α-Conotoxins

α-Conotoxins which bind to SCLC nicotinic receptors can be used for diagnosing SCLC tumors in patients. Suitable α-conotoxins include MII and U002. Administration of a labeled conotoxin to a patient will reveal the presence of SCLC cells if any are present. The α-conotoxin is labeled with a radioactive marker, preferably iodine, e.g., $^{131}I$ or $^{125}I$. Labeling can be performed by standard techniques well known in the art. The labeled toxin is administered intravenously in a range of 5–50 nmoles, preferably about 25 nmoles. The label is then detected by standard techniques well known in the art. The labeled toxins will bind to SCLC cells and also may bind to autonomic ganglia. However, the locations of autonomic ganglia are known and can be distinguished from signals resulting from binding of the labeled toxin to SCLC cells.

EXAMPLE 10

Therapeutic Use of α-Conotoxins to Treat SCLC Tumors

α-Conotoxins which bind to SCLC nicotinic receptors can be used therapeutically to treat patients with SCLC tumors. Suitable conotoxins are those which do not bind strongly to muscle receptors, e.g., MII and U002. Patients who have been diagnosed with SCLC can have a suitable conotoxin administered, preferably intravenously or intramuscularly. A dose of 200–2000 nanomoles, preferably about 500 nanomoles, is administered. The dosing schedule depends on the in vivo stability of the specific conotoxin used. In general conotoxins are relatively resistant to degradation and may last on the order of a few days. Therefore a typical dosing schedule may be anywhere from twice per day to once every few days, this being dependent on the biological lifetime of the specific conotoxin used.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

1. Olivera, B. M. et al. (1984). U.S. Pat. No. 4,447,356.

2. Olivera, B. M. et al. (1984). Purification and sequence of a presynaptic peptide toxin from *Conus geographus* venom. *Biochemistry*. 23:5087–90.

3. Sambrook, J. et al. (1979). *Molecular Cloning: A Laboratory Manual*, 2nd Ed., Cold Spring Harbor Laboratory, Cold Spring Harbor, N.Y.

4. Gray, W. R. (1993). Multicyclic cysteine peptides: a new method for disulfide analysis. Abstract, 13th American Peptide Symposium, Edmonton, Alberta.

5. "Methoden der Organischen Chemie (Houben-Weyl): Synthese von Peptiden," E. Wunsch (Ed.), Georg Thieme Verlag, Stuttgart, Ger. (1974).

6. Stewart and Young, *Solid-Phase Peptide Synthesis*, Freeman & Co., San Francisco, Calif. (1969).

7. Vale et al. (1978). U.S. Pat. No. 4,105,603.
8. U.S. Pat. No. 3,972,859 (1976).
9. U.S. Pat. No. 3,842,067 (1974).
10. U.S. Pat. No. 3,862,925 (1975).
11. Bodansky et al. (1966). *Chem. Ind.* 38:1597–98.
12. U.S. Pat. No. 4,569,967.
13. Horiki, K. et al. (1978). *Chemistry. Letters* 165–68.
14. Schroder & Lubke (1965). *The Peptides* 1:72–75, Academic Press, N.Y.
15. Kapoor (1970). *J. Pharm. Sci.* 59:1–27.
16. Kaiser et al. (1970). *Anal. Biochem.* 34:595.
17. Rivier, J. R. et al. (1978). *Biopolymers* 17:1927–38.
18. Zafarella, G. C. et al. (1988). *Biochemistry* 27: 7102–7105.

LIST OF REFERENCES (Cont'd)

19. Edman, P. & Begg (1967). *Eur. J. Blochem.* 1:80–91.
20. Merrifield, R. B. (1963). *J. Am. Chem. Soc.* 85: 2149–2154.
21. Gray, W. R. et al. (1983). *J. Biol. Chem.* 258: 12247–12251.
22. Tam, J. P. et al. (1983). *J. Am. Chem. Soc.* 105: 6442–6445.
23. Riviera, J. et al. (1984). *J. Chromatography* 288: 303–328.
24. Yoshikami, D. et al. (1989). The inhibitory effects of omega-conotoxins on calcium channels and synapses. *Ann. N.Y. Acad. Sci.* 560:230–48.
25. *PCR Technology*, H. A. Erlich, Ed., Stockton Press, New York, N.Y. (1989).
26. *PCR Protocols*, M. A. Innis, et al., Eds., Academic Press, San Diego, Calif. (1990).
27. Maneckjee, R. and Minna, J. D. (1990). *Proc. Natl. Acad. Sci. U.S.A.* 87: 3294–3298.
28. Chini, B. et al. (1992). *Proc. Natl. Acad. Sci. U.S.A.* 89: 1572–1576.
29. Tarroni, P. et al. (1992). *FEBS Lett.* 312: 66–70.
30. Schuller, H. M. et al. (1990). *Life Sci.* 47:571–578.
31. Cattaneo, M. G. et al. (1993). *Cancer Res.* 53: 5566–5568.
32. Codignola, A. et al. (1994). *FEBS Lett.* 342:286–290.
33. Farobrough, D. M. et al. (1973). *Science* 82:293–295.
34. U.S. Pat. No. 5,041,389.

What is claimed is:

1. A substanially pure κ-conotoxin peptide selected from the group consisting of:

Gln-Lys-Glu-Leu-Val-Pro-Ser-Val-Ile-Thr-Thr-Cys-Cys-Gly-Tyr-Asp-Pro-Gly-Thr-Met- Cys-Pro-Pro-Cys-Arg-Cys-Thr-Asn-Ser-Cys-Pro-Thr-Lys-Pro-Lys-Lys-Pro-Xaa$_1$ (SEQ ID NO:25), wherein Xaa$_1$ is des-Xaa$_1$ or Gly-Arg-Arg-Asn-Asp (SEQ ID NO:26);

Ala-Pro-Xaa$_1$-Leu-Val-Val-Thr-Ala-Thr-Thr-Asn-Cys-Cys-Gly-Tyr-Asn-Pro-Met-Thr-Ile- Cys-Pro-Pro-Cys-Met-Cys-Thr-Tyr-Ser-Cys-Pro-Pro-Lys-Arg-Lys-Pro-Xaa$_2$ (SEQ ID NO:27), wherein Xaa$_1$ is Glu or γ-carboxyglutamate and Xaa$_2$ is des-Xaa$_1$ or Gly-Arg-Arg-Asn-Asp (SEQ ID NO:26);

Glx-Thr-Trp-Leu-Val-Pro-Ser-Thr-Ile-Thr-Thr-Cys-Cys-Gly-Tyr-Asp-Pro-Gly-Thr-Met- Cys-Pro-Thr-Cys-Met-Cys-Asp-Asn-Thr-Cys-Lys-Pro-Lys-Pro-Lys-Lys-Ser-Xaa$_1$ (SEQ ID NO:28), wherein Xaa$_1$ is des-Xaa$_1$ or Gly-Arg-Arg-Asn-Asp (SEQ ID NO:26);

Ala-Pro-Trp-Leu-Val-Pro-Ser-Thr-Ile-Thr-Thr-Cys-Cys-Gly-Tyr-Asp-Pro-Gly-Ser-Met- Cys-Pro-Pro-Cys-Met-Cys-Asn-Asn-Thr-Cys-Lys-Pro-Lys-Pro-Lys-Lys-Ser-Xaa$_1$ (SEQ ID NO:29), wherein Xaa$_1$ is des-Xaa$_1$ or Gly-Arg-Arg-Asn-His (SEQ ID NO:30); and, Gly-Cys-Cys-Gly-Pro-Tyr-Xaa$_1$-Asn-Ala-Ala-Cys-His-Xaa$_2$-Cys-Gly-Cys-Lys-Val-Gly- Arg-Xaa$_3$-Xaa$_4$-Tyr-Cys-Asp-Arg-Xaa$_5$-Ser-Gly-Gly (SEQ ID NO:33), wherein Xaa$_1$, Xaa$_2$, Xaa$_3$, Xaa$_4$ and Xaa$_5$ are independently Pro or hydroxy-Pro.

2. The κ-conotoxin peptide of claim 1, having the sequence Gln-Lys-Glu-Leu-Val-Pro-Ser- Val-Ile-Thr-Thr-Cys-Cys-Gly-Tyr-Asp-Pro-Gly-Thr-Met-Cys-Pro-Pro-Cys-Arg-Cys-Thr- Asn-Ser-Cys-Pro-Thr-Lys-Pro-Lys-Lys-Pro-Xaa$_1$ (SEQ ID NO:25), wherein Xaa$_1$ is des-Xaa$_1$ or Gly-Arg-Arg-Asn-Asp (SEQ ID NO:26).

3. The κ-conotoxin of claim 2, wherein one or more of the Pro residues is hydroxy-Pro.

4. The κ-conotoxin peptide of claim 1, having the sequence Ala-Pro-Xaa$_1$-Leu-Val-Val-Thr- Ala-Thr-Thr-Asn-Cys-Cys-Gly-Tyr-Asn-Pro-Met-Thr-Ile-Cys-Pro-Pro-Cys-Met-Cys-Thr- Tyr-Ser-Cys-Pro-Pro-Lys-Arg-Lys-Pro-Xaa$_2$ (SEQ ID NO:27), wherein Xaa$_1$ is Glu or γ-carboxyglutamate and Xaa$_2$ is des-Xaa$_1$ or Gly-Arg-Arg-Asn-Asp (SEQ ID NO:26).

5. The κ-conotoxin of claim 4, wherein one or more of the Pro residues is hydroxy-Pro.

6. The κ-conotoxin peptide of claim 1, having the sequence Glx-Thr-Trp-Leu-Val-Pro-Ser- Thr-Ile-Thr-Thr-Cys-Cys-Gly-Tyr-Asp-Pro-Gly-Thr-Met-Cys-Pro-Thr-Cys-Met-Cys-Asp- Asn-Thr-Cys-Lys-Pro-Lys-Pro-Lys-Lys-Ser-Xaa$_1$ (SEQ ID NO:28), wherein Xaa$_1$ is des-Xaa$_1$ or Gly-Arg-Arg-Asn-Asp (SEQ ID NO:26).

7. The κ-conotoxin of claim 6, wherein one or more of the Pro residues is hydroxy-Pro.

8. The κ-conotoxin peptide of claim 1, having the sequence Ala-Pro-Trp-Leu-Val-Pro-Ser- Thr-Ile-Thr-Thr-Cys-Cys-Gly-Tyr-Asp-Pro-Gly-Ser-Met-Cys-Pro-Pro-Cys-Met-Cys-Asn- Asn-Thr-Cys-Lys-Pro-Lys-Pro-Lys-Lys-Ser-Xaa$_1$ (SEQ ID NO:29), wherein Xaa$_1$ is des-Xaa$_1$ or Gly-Arg-Arg-Asn-His (SEQ ID NO:30).

9. The κ-conotoxin of claim 8, wherein one or more of the Pro residues is hydroxy-Pro.

10. The κ-conotoxin of claim 1, having the sequence Gly-Cys-Cys-Gly-Pro-Tyr-Xaa$_1$- Asn-Ala-Ala-Cys-His-Xaa$_2$-Cys-Gly-Cys-Lys-Val-Gly-Arg-Xaa$_3$-Xaa$_4$-Tyr-Cys-Asp-Arg-Xaa$_5$- Ser-Gly-Gly (SEQ ID NO:33), wherein Xaa$_1$, Xaa$_2$, Xaa$_3$, Xaa$_4$ and Xaa$_5$ are independently Pro or hydroxy-Pro.

11. The κ-conotoxin of claim 10, wherein Xaa$_1$, Xaa$_2$, Xaa$_3$, Xaa$_4$ and Xaa$_5$ are Pro.

* * * * *

SEQUENCE LISTING ( 1 ) GENERAL INFORMATION:

( i i i ) NUMBER OF SEQUENCES: 59

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( v ) FRAGMENT TYPE: internal ( v i ) ORIGINAL SOURCE:
        ( A ) ORGANISM: Conus ( x i ) SEQUENCE DESCRIPTION: SEQ ID NO:1:

```
Cys  Cys  Xaa  Xaa  Xaa  Cys  Xaa  Xaa  Xaa  Xaa  Xaa  Cys
 1                  5                              10
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( v ) FRAGMENT TYPE: internal ( v i ) ORIGINAL SOURCE:
        ( A ) ORGANISM: Conus ( x i ) SEQUENCE DESCRIPTION: SEQ ID NO:2:

```
Cys Cys Xaa Xaa Xaa Xaa Cys Xaa Xaa Xaa Xaa Xaa Xaa Xaa Cys
1               5                   10                          15
```

( 2 ) INFORMATION FOR SEQ ID NO:3:

( i ) SEQUENCE CHARACTERISTICS:
        ( A ) LENGTH: 19 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( v ) FRAGMENT TYPE: internal ( v i ) ORIGINAL SOURCE:
        ( A ) ORGANISM: Conus ( x i ) SEQUENCE DESCRIPTION: SEQ ID NO:3:

```
Cys Cys Xaa Xaa Xaa Xaa Xaa Xaa Xaa Cys Xaa Xaa Cys Xaa Cys Xaa
1               5                   10                  15
Xaa Xaa Cys
```

( 2 ) INFORMATION FOR SEQ ID NO:4:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Conus geographus ( i x ) FEATURE:
        ( A ) NAME/KEY: Modified-site
        ( B ) LOCATION: 13
        ( D ) OTHER INFORMATION: /note= "The C-terminus is
            amidated."

( x i ) SEQUENCE DESCRIPTION: SEQ ID NO:4:

```
Glu Cys Cys Asn Pro Ala Cys Gly Arg His Tyr Ser Cys
1               5                   10
```

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Conus geographus ( x i ) SEQUENCE DESCRIPTION: SEQ ID NO:5:

```
Glu Cys Cys Asn Pro Ala Cys Gly Arg His Tyr Ser Cys Gly Lys
1               5                   10                  15
```

( 2 ) INFORMATION FOR SEQ ID NO:6:

( i ) SEQUENCE CHARACTERISTICS:
    ( A ) LENGTH: 13 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Conus geographus ( i x ) FEATURE:
    ( A ) NAME/KEY: Modified-site
    ( B ) LOCATION: 13
    ( D ) OTHER INFORMATION: /note= "The C-terminus is amidated."

( x i ) SEQUENCE DESCRIPTION: SEQ ID NO:6:

Glu Cys Cys His Pro Ala Cys Gly Lys His Phe Ser Cys
1               5                   10

( 2 ) INFORMATION FOR SEQ ID NO:7:

( i ) SEQUENCE CHARACTERISTICS:
    ( A ) LENGTH: 14 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Conus magus ( i x ) FEATURE:
    ( A ) NAME/KEY: Modified-site
    ( B ) LOCATION: 14
    ( D ) OTHER INFORMATION: /note= "The C-terminus is amidated."

( x i ) SEQUENCE DESCRIPTION: SEQ ID NO:7:

Gly Arg Cys Cys His Pro Ala Cys Gly Lys Asn Tyr Ser Cys
1               5                   10

( 2 ) INFORMATION FOR SEQ ID NO:8:

( i ) SEQUENCE CHARACTERISTICS:
    ( A ) LENGTH: 13 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Conus striatus ( i x ) FEATURE:
    ( A ) NAME/KEY: Modified-site
    ( B ) LOCATION: 13
    ( D ) OTHER INFORMATION: /note= "The C-terminus is amidated."

( x i ) SEQUENCE DESCRIPTION: SEQ ID NO:8:

Ile Cys Cys Asn Pro Ala Cys Gly Pro Lys Tyr Ser Cys
1               5                   10

( 2 ) INFORMATION FOR SEQ ID NO:9:

( i ) SEQUENCE CHARACTERISTICS:
 ( A ) LENGTH: 13 amino acids
 ( B ) TYPE: amino acid
 ( C ) STRANDEDNESS:
 ( D ) TOPOLOGY: linear ( i i ) MOLECULE TYPE: peptide ( i i i ) HYPOTHETICAL: NO ( v i ) ORIGINAL SOURCE:
 ( A ) ORGANISM: Conus striatus ( i x ) FEATURE:
 ( A ) NAME/KEY: Modified-site
 ( B ) LOCATION: 13
 ( D ) OTHER INFORMATION: /note= "The C-terminus is amidated."

( x i ) SEQUENCE DESCRIPTION: SEQ ID NO:9:

Tyr Cys Cys His Pro Ala Cys Gly Lys Asn Phe Asp Cys
1               5                   10

( 2 ) INFORMATION FOR SEQ ID NO:10:

( i ) SEQUENCE CHARACTERISTICS:
 ( A ) LENGTH: 20 amino acids
 ( B ) TYPE: amino acid
 ( C ) STRANDEDNESS:
 ( D ) TOPOLOGY: linear ( i i ) MOLECULE TYPE: peptide ( i i i ) HYPOTHETICAL: NO ( v i ) ORIGINAL SOURCE:
 ( A ) ORGANISM: Conus striatus ( i x ) FEATURE:
 ( A ) NAME/KEY: Modified-site
 ( B ) LOCATION: 20
 ( D ) OTHER INFORMATION: /note= "Xaa may be des-Xaa or Arg-Thr- Leu."

( x i ) SEQUENCE DESCRIPTION: SEQ ID NO:10:

Gly Cys Cys Cys Asn Pro Ala Cys Gly Pro Asn Tyr Gly Cys Gly Thr
1               5                   10                  15

Ser Cys Ser Xaa
        20

( 2 ) INFORMATION FOR SEQ ID NO:11:

( i ) SEQUENCE CHARACTERISTICS:
 ( A ) LENGTH: 12 amino acids
 ( B ) TYPE: amino acid
 ( C ) STRANDEDNESS:
 ( D ) TOPOLOGY: linear ( i i ) MOLECULE TYPE: peptide ( i i i ) HYPOTHETICAL: YES ( v ) FRAGMENT TYPE: internal ( v i ) ORIGINAL SOURCE:
 ( A ) ORGANISM: Conus ( i x ) FEATURE:
 ( A ) NAME/KEY: Modified-site
 ( B ) LOCATION: 3..10
 ( D ) OTHER INFORMATION: /note= "Xaa(3) is His or Asn; Xaa(10) is Tyr or Phe."

( x i ) SEQUENCE DESCRIPTION: SEQ ID NO:11:

```
Cys  Cys  Xaa  Pro  Ala  Cys  Gly  Xaa  Xaa  Xaa  Xaa  Cys
1                  5                        10
```

(2) INFORMATION FOR SEQ ID NO:12:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (iii) HYPOTHETICAL: NO (vi) ORIGINAL SOURCE:
        (A) ORGANISM: Conus imperialis (ix) FEATURE:
        (A) NAME/KEY: Modified-site
        (B) LOCATION: 12
        (D) OTHER INFORMATION: /note= "The C-terminus is
            preferably amidated."

(xi) SEQUENCE DESCRIPTION: SEQ ID NO:12:

```
Gly  Cys  Cys  Ser  Asp  Pro  Arg  Cys  Ala  Trp  Arg  Cys
1                  5                        10
```

(2) INFORMATION FOR SEQ ID NO:13:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (iii) HYPOTHETICAL: NO (vi) ORIGINAL SOURCE:
        (A) ORGANISM: Conus ermineus (ix) FEATURE:
        (A) NAME/KEY: Modified-site
        (B) LOCATION: 3
        (D) OTHER INFORMATION: /note= "Xaa is Pro or Hydroxy-Pro."

(xi) SEQUENCE DESCRIPTION: SEQ ID NO:13:

```
Arg  Asp  Xaa  Cys  Cys  Tyr  His  Pro  Thr  Cys  Asn  Met  Ser  Asn  Pro  Gln
1                  5                        10                       15

Ile  Cys
```

(2) INFORMATION FOR SEQ ID NO:14:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (iii) HYPOTHETICAL: NO (vi) ORIGINAL SOURCE:
        (A) ORGANISM: Conus bandanus (ix) FEATURE:
        (A) NAME/KEY: Modified-site
        (B) LOCATION: 6..14
        (D) OTHER INFORMATION: /note= "Xaa(6) is Pro or
            Hydroxy-Pro; Xaa(13) is Pro or Hydroxy-Pro; Xaa(14) is Asp or beta-carboxyaspartate."

( i x ) FEATURE:
    ( A ) NAME/KEY: Modified-site
    ( B ) LOCATION: 16
    ( D ) OTHER INFORMATION: /note= "The C-terminus is
        preferably amidated."

( x i ) SEQUENCE DESCRIPTION: SEQ ID NO:14:

Gly Cys Cys Ser His Xaa Ala Cys Ser Val Asn Asn Xaa Xaa Ile Cys
1               5                   10                  15

( 2 ) INFORMATION FOR SEQ ID NO:15:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Conus bandanus ( i x ) FEATURE:
        ( A ) NAME/KEY: Modified-site
        ( B ) LOCATION: 16
        ( D ) OTHER INFORMATION: /note= "The C-terminus is
            preferably amidated."

( i x ) FEATURE:
        ( A ) NAME/KEY: Modified-site
        ( B ) LOCATION: 6..13
        ( D ) OTHER INFORMATION: /note= "Xaa(6) is Pro or
            Hydroxy-Pro; Xaa(13) is Pro or Hydroxy-Pro."

( x i ) SEQUENCE DESCRIPTION: SEQ ID NO:15:

Glu Cys Cys Thr His Xaa Ala Cys His Val Ser His Xaa Glu Leu Cys
1               5                   10                  15

( 2 ) INFORMATION FOR SEQ ID NO:16:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Conus bandanus ( i x ) FEATURE:
        ( A ) NAME/KEY: Modified-site
        ( B ) LOCATION: 13
        ( D ) OTHER INFORMATION: /note= "The C-terminus is
            preferably amidated."

( x i ) SEQUENCE DESCRIPTION: SEQ ID NO:16:

Asp Tyr Cys Cys His Arg Gly Pro Cys Met Val Trp Cys
1               5                   10

( 2 ) INFORMATION FOR SEQ ID NO:17:

( i ) SEQUENCE CHARACTERISTICS:
        ( A ) LENGTH: 16 amino acids
        ( B ) TYPE: amino acid
        ( C ) STRANDEDNESS:

( D ) TOPOLOGY: linear ( i i ) MOLECULE TYPE: peptide ( i i i ) HYPOTHETICAL: NO ( v i ) ORIGINAL SOURCE:
    ( A ) ORGANISM: Conus caracteristicus ( i x ) FEATURE:
    ( A ) NAME/KEY: Modified-site
    ( B ) LOCATION: 16
    ( D ) OTHER INFORMATION: /note= "Xaa is Ser or Asn."

( x i ) SEQUENCE DESCRIPTION: SEQ ID NO:17:

```
Gln Asn Cys Cys Ser Ile Pro Ser Cys Trp Glu Lys Tyr Lys Cys Xaa
1               5                   10                  15
```

( 2 ) INFORMATION FOR SEQ ID NO:18:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Conus caracteristicus ( x i ) SEQUENCE DESCRIPTION: SEQ ID NO:18:

```
Gly Cys Cys Ala Ile Arg Glu Cys Arg Leu Gln Asn Ala Ala Tyr Cys
1               5                   10                  15
Gly Gly Ile Tyr
                20
```

( 2 ) INFORMATION FOR SEQ ID NO:19:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Conus magus ( i x ) FEATURE:
    ( A ) NAME/KEY: Modified-site
    ( B ) LOCATION: 6
    ( D ) OTHER INFORMATION: /note= "Xaa is Pro or Hydroxy-Pro."

( i x ) FEATURE:
    ( A ) NAME/KEY: Modified-site
    ( B ) LOCATION: 16
    ( D ) OTHER INFORMATION: /note= "The C-terminus is
        preferably amidated."

( x i ) SEQUENCE DESCRIPTION: SEQ ID NO:19:

```
Gly Cys Cys Ser Asn Xaa Val Cys His Leu Glu His Ser Asn Leu Cys
1               5                   10                  15
```

( 2 ) INFORMATION FOR SEQ ID NO:20:

( i ) SEQUENCE CHARACTERISTICS:
        ( A ) LENGTH: 18 amino acids (B) TYPE: amino acid
(C) STRANDEDNESS:
(D) TOPOLOGY: linear (i i) MOLECULE TYPE: peptide (i i i) HYPOTHETICAL: NO (v i) ORIGINAL SOURCE:
(A) ORGANISM: Conus sulcatus (i x) FEATURE:
(A) NAME/KEY: Modified-site
(B) LOCATION: 7..15
(D) OTHER INFORMATION: /note= "Xaa(7) is Pro or Hydroxy-Pro; Xaa(14) is Pro or Hydroxy-Pro; Xaa(15) is Glu or gamma-carboxyglutamate"

(i x) FEATURE:
(A) NAME/KEY: Modified-site
(B) LOCATION: 18
(D) OTHER INFORMATION: /note= "The C-terminus is preferably amidated."

(x i) SEQUENCE DESCRIPTION: SEQ ID NO:20:

```
Gly Gly Cys Cys Ser Phe Xaa Ala Cys Arg Lys Tyr Arg Xaa Xaa Met
1               5                   10                  15
Cys Gly
```

(2) INFORMATION FOR SEQ ID NO:21:

(i) SEQUENCE CHARACTERISTICS:
(A) LENGTH: 19 amino acids
(B) TYPE: amino acid
(C) STRANDEDNESS:
(D) TOPOLOGY: linear (i i) MOLECULE TYPE: peptide (i i i) HYPOTHETICAL: NO (v i) ORIGINAL SOURCE:
(A) ORGANISM: Conus sulcatus (i x) FEATURE:
(A) NAME/KEY: Modified-site
(B) LOCATION: 6..14
(D) OTHER INFORMATION: /note= "Xaa(6) is Pro or Hydroxy-Pro; Xaa(13) is Pro or Hydroxy-Pro; Xaa(14) is Glu or gamma-carboxyglutamate"

(i x) FEATURE:
(A) NAME/KEY: Modified-site
(B) LOCATION: 19
(D) OTHER INFORMATION: /note= "The C-terminus is preferably amidated."

(x i) SEQUENCE DESCRIPTION: SEQ ID NO:21:

```
Ala Cys Cys Ser Tyr Xaa Pro Cys Asn Val Asn Tyr Xaa Xaa Ile Cys
1               5                   10                  15
Gly Gly Arg
```

(2) INFORMATION FOR SEQ ID NO:22:

(i) SEQUENCE CHARACTERISTICS:
(A) LENGTH: 15 amino acids
(B) TYPE: amino acid
(C) STRANDEDNESS:
(D) TOPOLOGY: linear (i i) MOLECULE TYPE: peptide (i i i) HYPOTHETICAL: NO (vi) ORIGINAL SOURCE:
 (A) ORGANISM: Conus striatus (xi) SEQUENCE DESCRIPTION: SEQ ID NO:22:

Asn Gly Cys Cys Arg Asn Pro Ala Cys Glu Ser His Arg Cys Gly
1               5                   10                  15

(2) INFORMATION FOR SEQ ID NO:23:

(i) SEQUENCE CHARACTERISTICS:
  (A) LENGTH: 42 amino acids
  (B) TYPE: amino acid
  (C) STRANDEDNESS:
  (D) TOPOLOGY: linear (ii) MOLECULE TYPE: peptide (iii) HYPOTHETICAL: NO (vi) ORIGINAL SOURCE:
  (A) ORGANISM: Conus ochroleucus (xi) SEQUENCE DESCRIPTION: SEQ ID NO:23:

Asn Val Val Val Thr Ser Phe Glu Pro Thr Thr Leu Ala Pro Val Pro
1               5                   10                  15

Ser Asp Cys Cys Gln Val Ser Ser Cys Trp Asn Leu Tyr Gly Leu Glu
            20                  25                  30

Cys Thr Gly Ile Thr Arg Arg Arg Thr Leu
            35              40

(2) INFORMATION FOR SEQ ID NO:24:

(i) SEQUENCE CHARACTERISTICS:
  (A) LENGTH: 42 amino acids
  (B) TYPE: amino acid
  (C) STRANDEDNESS:
  (D) TOPOLOGY: linear (ii) MOLECULE TYPE: peptide (iii) HYPOTHETICAL: NO (vi) ORIGINAL SOURCE:
  (A) ORGANISM: Conus ochroleucus (xi) SEQUENCE DESCRIPTION: SEQ ID NO:24:

Asn Val Ala Ile Thr Ser Phe Glu Pro Thr Thr Leu Ala Pro Val Pro
1               5                   10                  15

Ser Asp Cys Cys Gln Val Ser Ser Cys Trp Asn Leu Tyr Gly Pro Glu
            20                  25                  30

Cys Thr Gly Ile Thr Arg Arg Arg Thr Leu
            35              40

(2) INFORMATION FOR SEQ ID NO:25:

(i) SEQUENCE CHARACTERISTICS:
  (A) LENGTH: 38 amino acids
  (B) TYPE: amino acid
  (C) STRANDEDNESS:
  (D) TOPOLOGY: linear (ii) MOLECULE TYPE: peptide (iii) HYPOTHETICAL: NO (vi) ORIGINAL SOURCE:
  (A) ORGANISM: Conus striatus (ix) FEATURE:
  (A) NAME/KEY: Modified-site (B) LOCATION: 38
            (D) OTHER INFORMATION: /note= "Xaa is des-Xaa or
                   Gly-Arg-Arg- Asn-Asp."

(ix) FEATURE:
            (A) NAME/KEY: Modified-site
            (B) LOCATION: 38
            (D) OTHER INFORMATION: /note= "When the C-terminus is
                   des-Xaa it is preferably amidated."

(xi) SEQUENCE DESCRIPTION: SEQ ID NO:25:

```
Gln  Lys  Glu  Leu  Val  Pro  Ser  Val  Ile  Thr  Thr  Cys  Cys  Gly  Tyr  Asp
1                   5                        10                       15

Pro  Gly  Thr  Met  Cys  Pro  Pro  Cys  Arg  Cys  Thr  Asn  Ser  Cys  Pro  Thr
                20                       25                       30

Lys  Pro  Lys  Lys  Pro  Xaa
                35
```

(2) INFORMATION FOR SEQ ID NO:26:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: C-terminal (vi) ORIGINAL SOURCE:
            (A) ORGANISM: Conus striatus (xi) SEQUENCE DESCRIPTION: SEQ ID NO:26:

```
Gly  Arg  Arg  Asn  Asp
1                   5
```

(2) INFORMATION FOR SEQ ID NO:27:

(i) SEQUENCE CHARACTERISTICS:
            (A) LENGTH: 37 amino acids
            (B) TYPE: amino acid
            (C) STRANDEDNESS:
            (D) TOPOLOGY: linear (ii) MOLECULE TYPE: peptide (iii) HYPOTHETICAL: NO (vi) ORIGINAL SOURCE:
            (A) ORGANISM: Conus magus (ix) FEATURE:
            (A) NAME/KEY: Modified-site
            (B) LOCATION: 3
            (D) OTHER INFORMATION: /note= "Amino acid 3 is either Glu
                   or gamma- carboxyglutamate."

(ix) FEATURE:
            (A) NAME/KEY: Modified-site
            (B) LOCATION: 37
            (D) OTHER INFORMATION: /note= "Xaa is des-Xaa or
                   Gly-Arg-Arg- Asn-Asp. When Xaa is des-Xaa the C-terminus
                   is preferably amidated."

(xi) SEQUENCE DESCRIPTION: SEQ ID NO:27:

```
Ala  Pro  Glu  Leu  Val  Val  Thr  Ala  Thr  Thr  Asn  Cys  Cys  Gly  Tyr  Asn
1                   5                        10                       15

Pro  Met  Thr  Ile  Cys  Pro  Pro  Cys  Met  Cys  Thr  Tyr  Ser  Cys  Pro  Pro
                20                       25                       30
```

Lys Arg Lys Pro Xaa
            35

( 2 ) INFORMATION FOR SEQ ID NO:28:

( i ) SEQUENCE CHARACTERISTICS:
         ( A ) LENGTH: 38 amino acids
         ( B ) TYPE: amino acid
         ( C ) STRANDEDNESS:
         ( D ) TOPOLOGY: linear ( i i ) MOLECULE TYPE: peptide ( i i i ) HYPOTHETICAL: NO ( v i ) ORIGINAL SOURCE:
         ( A ) ORGANISM: Conus stercusmuscarum ( i x ) FEATURE:
         ( A ) NAME/KEY: Modified-site
         ( B ) LOCATION: 38
         ( D ) OTHER INFORMATION: /note= "Xaa is des-Xaa or
               Gly-Arg-Arg- Asn-Asp. When Xaa is des-Xaa the C-terminus
               is preferably amidated."

( x i ) SEQUENCE DESCRIPTION: SEQ ID NO:28:

Glx Thr Trp Leu Val Pro Ser Thr Ile Thr Thr Cys Cys Gly Tyr Asp
1               5                   10                  15

Pro Gly Thr Met Cys Pro Thr Cys Met Cys Asp Asn Thr Cys Lys Pro
            20              25                  30

Lys Pro Lys Lys Ser Xaa
            35

( 2 ) INFORMATION FOR SEQ ID NO:29:

( i ) SEQUENCE CHARACTERISTICS:
         ( A ) LENGTH: 38 amino acids
         ( B ) TYPE: amino acid
         ( C ) STRANDEDNESS:
         ( D ) TOPOLOGY: linear ( i i ) MOLECULE TYPE: peptide ( i i i ) HYPOTHETICAL: NO ( v i ) ORIGINAL SOURCE:
         ( A ) ORGANISM: Conus stercusmuscarum ( i x ) FEATURE:
         ( A ) NAME/KEY: Modified-site
         ( B ) LOCATION: 38
         ( D ) OTHER INFORMATION: /note= "Xaa is des-Xaa or
               Gly-Arg-Arg- Asn-His. When Xaa is des-Xaa the C-terminus
               is preferably amidated."

( x i ) SEQUENCE DESCRIPTION: SEQ ID NO:29:

Ala Pro Trp Leu Val Pro Ser Thr Ile Thr Thr Cys Cys Gly Tyr Asp
1               5                   10                  15

Pro Gly Ser Met Cys Pro Pro Cys Met Cys Asn Asn Thr Cys Lys Pro
            20              25                  30

Lys Pro Lys Lys Ser Xaa
            35

( 2 ) INFORMATION FOR SEQ ID NO:30:

( i ) SEQUENCE CHARACTERISTICS:
         ( A ) LENGTH: 5 amino acids
         ( B ) TYPE: amino acid
         ( C ) STRANDEDNESS:
         ( D ) TOPOLOGY: linear ( i i ) MOLECULE TYPE: peptide ( i i i ) HYPOTHETICAL: NO ( v ) FRAGMENT TYPE: C-terminal ( v i ) ORIGINAL SOURCE:
    ( A ) ORGANISM: Conus stercusmuscarum ( x i ) SEQUENCE DESCRIPTION: SEQ ID NO:30:

Gly Arg Arg Asn His
1               5

( 2 ) INFORMATION FOR SEQ ID NO:31:

( i ) SEQUENCE CHARACTERISTICS:
    ( A ) LENGTH: 18 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Conus ermineus ( i x ) FEATURE:
    ( A ) NAME/KEY: Modified-site
    ( B ) LOCATION: 3
    ( D ) OTHER INFORMATION: /note= "Xaa is Pro or Hydroxy-Pro."

( i x ) FEATURE:
    ( A ) NAME/KEY: Modified-site
    ( B ) LOCATION: 18
    ( D ) OTHER INFORMATION: /note= "The C-terminus is
        preferably amidated."

( x i ) SEQUENCE DESCRIPTION: SEQ ID NO:31:

Arg Asp Xaa Cys Cys Tyr His Pro Thr Cys Asn Met Ser Asn Pro Gln
1               5                   10                  15

Ile Cys ( 2 ) INFORMATION FOR SEQ ID NO:32:

( i ) SEQUENCE CHARACTERISTICS:
    ( A ) LENGTH: 18 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Conus ermineus ( i x ) FEATURE:
    ( A ) NAME/KEY: Modified-site
    ( B ) LOCATION: 3
    ( D ) OTHER INFORMATION: /note= "Xaa is Pro or Hydroxy-Pro."

( i x ) FEATURE:
    ( A ) NAME/KEY: Modified-site
    ( B ) LOCATION: 18
    ( D ) OTHER INFORMATION: /note= "The C-terminus is
        preferably amidated."

( x i ) SEQUENCE DESCRIPTION: SEQ ID NO:32:

Arg Asp Xaa Cys Cys Ser Asn Pro Ala Cys Asn Val Asn Asn Pro Gln
1               5                   10                  15

Ile Cys (2) INFORMATION FOR SEQ ID NO:33:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (iii) HYPOTHETICAL: NO (vi) ORIGINAL SOURCE:
        (A) ORGANISM: Conus ermineus (ix) FEATURE:
        (A) NAME/KEY: Modified-site
        (B) LOCATION: 7
        (D) OTHER INFORMATION: /note= "Amino acid 7 is Pro or
            Hydroxy- Pro."

(ix) FEATURE:
        (A) NAME/KEY: Modified-site
        (B) LOCATION: 27
        (D) OTHER INFORMATION: /note= "Amino acid 27 is Pro or
            Hydroxy- Pro."

(xi) SEQUENCE DESCRIPTION: SEQ ID NO:33:

Gly Cys Cys Gly Pro Tyr Xaa Asn Ala Ala Cys His Xaa Cys Gly Cys
    1               5                   10                  15

Lys Val Gly Arg Xaa Xaa Tyr Cys Asp Arg Xaa Ser Gly Gly
                20                  25                  30

(2) INFORMATION FOR SEQ ID NO:34:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (iii) HYPOTHETICAL: NO (vi) ORIGINAL SOURCE:
        (A) ORGANISM: Conus striatus (ix) FEATURE:
        (A) NAME/KEY: Modified-site
        (B) LOCATION: 14
        (D) OTHER INFORMATION: /note= "The C-terminus is
            amidated."

(xi) SEQUENCE DESCRIPTION: SEQ ID NO:34:

Glu Ile Cys Cys Asn Pro Ala Cys Gly Pro Lys Tyr Ser Cys
    1               5                   10

(2) INFORMATION FOR SEQ ID NO:35:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (iii) HYPOTHETICAL: NO (vi) ORIGINAL SOURCE:

(A) ORGANISM: Conus striatus (ix) FEATURE:
    (A) NAME/KEY: Modified-site
    (B) LOCATION: 30
    (D) OTHER INFORMATION: /note= "The C-terminus is amidated."

(xi) SEQUENCE DESCRIPTION: SEQ ID NO:35:

```
Gln Lys Ser Leu Val Pro Ser Val Ile Thr Thr Cys Cys Gly Tyr Asp
 1               5                   10                  15
Pro Gly Thr Met Cys Pro Pro Cys Arg Cys Thr Asn Ser Cys
                20              25                  30
```

(2) INFORMATION FOR SEQ ID NO:36:

(i) SEQUENCE CHARACTERISTICS:
        (A) LENGTH: 64 amino acids
        (B) TYPE: amino acid
        (C) STRANDEDNESS:
        (D) TOPOLOGY: linear (ii) MOLECULE TYPE: peptide (iii) HYPOTHETICAL: NO (vi) ORIGINAL SOURCE:
        (A) ORGANISM: Conus geographus (xi) SEQUENCE DESCRIPTION: SEQ ID NO:36:

```
Met Gly Met Arg Met Met Phe Thr Val Phe Leu Leu Val Val Leu Ala
 1               5                   10                  15
Thr Thr Val Val Ser Phe Pro Ser Glu Arg Ala Ser Asp Gly Arg Asp
                20              25                  30
Asp Thr Ala Lys Asp Glu Gly Ser Asp Met Glu Lys Leu Val Glu Lys
                35              40                  45
Lys Glu Cys Cys Asn Pro Ala Cys Gly Arg His Tyr Ser Cys Gly Arg
     50              55                  60
```

(2) INFORMATION FOR SEQ ID NO:37:

(i) SEQUENCE CHARACTERISTICS:
        (A) LENGTH: 64 amino acids
        (B) TYPE: amino acid
        (C) STRANDEDNESS:
        (D) TOPOLOGY: linear (ii) MOLECULE TYPE: peptide (iii) HYPOTHETICAL: NO (vi) ORIGINAL SOURCE:
        (A) ORGANISM: Conus striatus (xi) SEQUENCE DESCRIPTION: SEQ ID NO:37:

```
Met Gly Met Arg Met Met Phe Thr Val Phe Leu Leu Val Val Leu Ala
 1               5                   10                  15
Thr Thr Val Val Ser Phe Pro Ser Asp Arg Ala Ser Asp Gly Arg Asp
                20              25                  30
Asp Glu Ala Lys Asp Glu Arg Ser Asp Met His Glu Ser Asp Arg Lys
                35              40                  45
Glu Ile Cys Cys Asn Pro Ala Cys Gly Pro Lys Tyr Ser Cys Gly Arg
     50              55                  60
```

(2) INFORMATION FOR SEQ ID NO:38:

(i) SEQUENCE CHARACTERISTICS:

(A) LENGTH: 72 amino acids
(B) TYPE: amino acid
(C) STRANDEDNESS:
(D) TOPOLOGY: linear (ii) MOLECULE TYPE: peptide (iii) HYPOTHETICAL: NO (vi) ORIGINAL SOURCE:
(A) ORGANISM: Conus striatus (xi) SEQUENCE DESCRIPTION: SEQ ID NO:38:

| Met | Gly | Met | Arg | Met | Met | Phe | Thr | Val | Phe | Leu | Leu | Val | Val | Leu | Ala |
|---|---|---|---|---|---|---|---|---|---|---|---|---|---|---|---|
| 1 | | | | 5 | | | | | 10 | | | | | 15 | |

| Thr | Thr | Val | Val | Ser | Phe | Pro | Ser | Asp | Arg | Ala | Ser | Asp | Gly | Arg | Asp |
|---|---|---|---|---|---|---|---|---|---|---|---|---|---|---|---|
| | | | 20 | | | | | 25 | | | | | 30 | | |

| Asp | Glu | Ala | Lys | Asp | Glu | Arg | Ser | Asp | Met | His | Glu | Ser | Asp | Arg | Asn |
|---|---|---|---|---|---|---|---|---|---|---|---|---|---|---|---|
| | | | 35 | | | | | 40 | | | | | 45 | | |

| Gly | Arg | Gly | Cys | Cys | Cys | Asn | Pro | Ala | Cys | Gly | Pro | Asn | Tyr | Gly | Cys |
|---|---|---|---|---|---|---|---|---|---|---|---|---|---|---|---|
| | 50 | | | | | 55 | | | | | 60 | | | | |

| Gly | Thr | Ser | Cys | Ser | Arg | Thr | Leu |
|---|---|---|---|---|---|---|---|
| 65 | | | | | 70 | | |

(2) INFORMATION FOR SEQ ID NO:39:

(i) SEQUENCE CHARACTERISTICS:
(A) LENGTH: 64 amino acids
(B) TYPE: amino acid
(C) STRANDEDNESS:
(D) TOPOLOGY: linear (ii) MOLECULE TYPE: peptide (iii) HYPOTHETICAL: NO (vi) ORIGINAL SOURCE:
(A) ORGANISM: Conus striatus (xi) SEQUENCE DESCRIPTION: SEQ ID NO:39:

| Met | Gly | Met | Arg | Met | Met | Phe | Thr | Val | Phe | Leu | Leu | Val | Val | Leu | Ala |
|---|---|---|---|---|---|---|---|---|---|---|---|---|---|---|---|
| 1 | | | | 5 | | | | | 10 | | | | | 15 | |

| Thr | Thr | Val | Val | Ser | Phe | Pro | Ser | Asp | Arg | Ala | Ser | Asp | Gly | Arg | Asp |
|---|---|---|---|---|---|---|---|---|---|---|---|---|---|---|---|
| | | | 20 | | | | | 25 | | | | | 30 | | |

| Asp | Glu | Ala | Lys | Asp | Glu | Arg | Ser | Asp | Met | His | Glu | Ser | Asp | Arg | Lys |
|---|---|---|---|---|---|---|---|---|---|---|---|---|---|---|---|
| | | | 35 | | | | | 40 | | | | | 45 | | |

| Glu | Ile | Cys | Cys | Asn | Pro | Ala | Cys | Gly | Pro | Lys | Tyr | Ser | Cys | Gly | Arg |
|---|---|---|---|---|---|---|---|---|---|---|---|---|---|---|---|
| | 50 | | | | | 55 | | | | | 60 | | | | |

(2) INFORMATION FOR SEQ ID NO:40:

(i) SEQUENCE CHARACTERISTICS:
(A) LENGTH: 69 amino acids
(B) TYPE: amino acid
(C) STRANDEDNESS:
(D) TOPOLOGY: linear (ii) MOLECULE TYPE: peptide (iii) HYPOTHETICAL: NO (vi) ORIGINAL SOURCE:
(A) ORGANISM: Conus striatus (xi) SEQUENCE DESCRIPTION: SEQ ID NO:40:

| Met | Gly | Met | Arg | Met | Met | Phe | Thr | Val | Phe | Leu | Leu | Val | Val | Leu | Ala |
|---|---|---|---|---|---|---|---|---|---|---|---|---|---|---|---|
| 1 | | | | 5 | | | | | 10 | | | | | 15 | |

```
Thr  Asn  Val  Val  Ser  Thr  Pro  Ser  Asp  Arg  Ala  Ser  Asp  Gly  Arg  Asn
          20                      25                      30

Ala  Ala  Val  His  Glu  Arg  Gln  Lys  Ser  Leu  Val  Pro  Ser  Val  Ile  Thr
          35                      40                      45

Thr  Cys  Cys  Gly  Tyr  Asp  Pro  Gly  Thr  Met  Cys  Pro  Pro  Cys  Arg  Cys
     50                      55                      60

Thr  Asn  Ser  Cys  Gly
65
```

( 2 ) INFORMATION FOR SEQ ID NO:41:

( i ) SEQUENCE CHARACTERISTICS:
        ( A ) LENGTH: 80 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Conus striatus ( x i ) SEQUENCE DESCRIPTION: SEQ ID NO:41:

```
Met  Gly  Met  Arg  Met  Met  Phe  Thr  Val  Phe  Leu  Ser  Val  Val  Leu  Ala
1              5                      10                      15

Thr  Thr  Val  Val  Ser  Thr  Pro  Ser  Asp  Arg  Ala  Ser  Asp  Gly  Arg  Asn
          20                      25                      30

Ala  Ala  Val  His  Glu  Arg  Gln  Lys  Glu  Leu  Val  Pro  Ser  Val  Ile  Thr
          35                      40                      45

Thr  Cys  Cys  Gly  Tyr  Asp  Pro  Gly  Thr  Met  Cys  Pro  Pro  Cys  Arg  Cys
     50                      55                      60

Thr  Asn  Ser  Cys  Pro  Thr  Lys  Pro  Lys  Lys  Pro  Gly  Arg  Arg  Asn  Asp
65                       70                      75                       80
```

( 2 ) INFORMATION FOR SEQ ID NO:42:

( i ) SEQUENCE CHARACTERISTICS:
        ( A ) LENGTH: 79 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Conus magus ( x i ) SEQUENCE DESCRIPTION: SEQ ID NO:42:

```
Met  Gly  Met  Arg  Met  Met  Phe  Thr  Val  Phe  Leu  Leu  Val  Val  Leu  Ala
1              5                      10                      15

Thr  Thr  Val  Val  Ser  Ile  Pro  Ser  Asp  Arg  Ala  Ser  Asp  Gly  Arg  Asn
          20                      25                      30

Ala  Val  Val  His  Glu  Arg  Ala  Pro  Glu  Leu  Val  Val  Thr  Ala  Thr  Thr
          35                      40                      45

Asn  Cys  Cys  Gly  Tyr  Asn  Pro  Met  Thr  Ile  Cys  Pro  Pro  Cys  Met  Cys
     50                      55                      60

Thr  Tyr  Ser  Cys  Pro  Pro  Lys  Arg  Lys  Pro  Gly  Arg  Arg  Asn  Asp
65                       70                      75
```

( 2 ) INFORMATION FOR SEQ ID NO:43:

( i ) SEQUENCE CHARACTERISTICS:
- ( A ) LENGTH: 80 amino acids
- ( B ) TYPE: amino acid
- ( C ) STRANDEDNESS:
- ( D ) TOPOLOGY: linear ( i i ) MOLECULE TYPE: peptide ( i i i ) HYPOTHETICAL: NO ( v i ) ORIGINAL SOURCE:
- ( A ) ORGANISM: Conus stercusmuscarum ( x i ) SEQUENCE DESCRIPTION: SEQ ID NO:43:

```
Met Gly Met Arg Met Met Phe Thr Val Phe Leu Leu Val Val Leu Ala
1               5                   10                      15

Thr Thr Val Val Ser Ile Pro Ser Asp Arg Ala Ser Asp Gly Arg Asn
            20              25                  30

Ala Ala Val Asn Glu Arg Gln Thr Trp Leu Val Pro Ser Thr Ile Thr
            35              40                  45

Thr Cys Cys Gly Tyr Asp Pro Gly Thr Met Cys Pro Thr Cys Met Cys
    50              55                  60

Asp Asn Thr Cys Lys Pro Lys Pro Lys Lys Ser Gly Arg Arg Asn Asp
65              70              75                              80
```

( 2 ) INFORMATION FOR SEQ ID NO:44:

( i ) SEQUENCE CHARACTERISTICS:
- ( A ) LENGTH: 80 amino acids
- ( B ) TYPE: amino acid
- ( C ) STRANDEDNESS:
- ( D ) TOPOLOGY: linear ( i i ) MOLECULE TYPE: peptide ( i i i ) HYPOTHETICAL: NO ( v i ) ORIGINAL SOURCE:
- ( A ) ORGANISM: Conus stercusmuscarum ( x i ) SEQUENCE DESCRIPTION: SEQ ID NO:44:

```
Met Gly Met Arg Met Met Phe Thr Val Phe Leu Leu Val Val Leu Ala
1               5                   10                      15

Thr Thr Val Val Ser Ile Pro Ser Asp Arg Ala Ser Asp Gly Arg Asn
            20              25                  30

Ala Glu Val Asn Glu Arg Ala Pro Trp Leu Val Pro Ser Thr Ile Thr
            35              40                  45

Thr Cys Cys Gly Tyr Asp Pro Gly Ser Met Cys Pro Pro Cys Met Cys
    50              55                  60

Asn Asn Thr Cys Lys Pro Lys Pro Lys Lys Ser Gly Arg Arg Asn His
65              70              75                              80
```

( 2 ) INFORMATION FOR SEQ ID NO:45:

( i ) SEQUENCE CHARACTERISTICS:
- ( A ) LENGTH: 64 amino acids
- ( B ) TYPE: amino acid
- ( C ) STRANDEDNESS:
- ( D ) TOPOLOGY: linear ( i i ) MOLECULE TYPE: peptide ( i i i ) HYPOTHETICAL: NO ( v i ) ORIGINAL SOURCE:
- ( A ) ORGANISM: Conus geographus ( x i ) SEQUENCE DESCRIPTION: SEQ ID NO:45:

| Met | Gly | Met | Arg | Met | Met | Phe | Thr | Val | Phe | Leu | Leu | Val | Val | Leu | Ala |
| 1 | | | | 5 | | | | | 10 | | | | | 15 | |

| Thr | Thr | Val | Val | Ser | Phe | Pro | Ser | Glu | Arg | Ala | Ser | Asp | Gly | Arg | Asp |
| | | | 20 | | | | | 25 | | | | | 30 | | |

| Asp | Thr | Ala | Lys | Asp | Glu | Gly | Ser | Asp | Met | Glu | Lys | Leu | Val | Glu | Lys |
| | | 35 | | | | | 40 | | | | | 45 | | | |

| Lys | Glu | Cys | Cys | Asn | Pro | Ala | Cys | Gly | Arg | His | Tyr | Ser | Cys | Gly | Arg |
| | 50 | | | | | 55 | | | | | 60 | | | | |

( 2 ) INFORMATION FOR SEQ ID NO:46:

( i ) SEQUENCE CHARACTERISTICS:
        ( A ) LENGTH: 65 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Conus bandanus ( x i ) SEQUENCE DESCRIPTION: SEQ ID NO:46:

| Met | Gly | Met | Arg | Met | Met | Phe | Thr | Met | Phe | Leu | Leu | Val | Val | Leu | Ala |
| 1 | | | | 5 | | | | | 10 | | | | | 15 | |

| Thr | Thr | Val | Val | Ser | Phe | Ala | Ser | Asp | Arg | Ala | Ser | Asp | Gly | Arg | Asn |
| | | | 20 | | | | | 25 | | | | | 30 | | |

| Ala | Ala | Ala | Lys | Asp | Lys | Ala | Ser | Asp | Leu | Val | Ala | Leu | Thr | Val | Lys |
| | | 35 | | | | | 40 | | | | | 45 | | | |

| Gly | Cys | Cys | Ser | His | Pro | Ala | Cys | Ser | Val | Asn | Asn | Pro | Asp | Ile | Cys |
| | 50 | | | | | 55 | | | | | 60 | | | | |

| Gly |
| 65 |

( 2 ) INFORMATION FOR SEQ ID NO:47:

( i ) SEQUENCE CHARACTERISTICS:
        ( A ) LENGTH: 68 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Conus caracteristicus ( x i ) SEQUENCE DESCRIPTION: SEQ ID NO:47:

| Met | Gly | Met | Arg | Met | Met | Phe | Thr | Val | Phe | Leu | Leu | Val | Val | Leu | Ala |
| 1 | | | | 5 | | | | | 10 | | | | | 15 | |

| Thr | Thr | Val | Val | Ser | Phe | Thr | Ser | Asp | Arg | Ala | Ser | Glu | Gly | Arg | Asn |
| | | | 20 | | | | | 25 | | | | | 30 | | |

| Ala | Ala | Ala | Lys | Asp | Lys | Ala | Ser | Asp | Leu | Val | Ala | Leu | Thr | Val | Arg |
| | | 35 | | | | | 40 | | | | | 45 | | | |

| Gly | Cys | Cys | Ala | Ile | Arg | Glu | Cys | Arg | Leu | Gln | Asn | Ala | Ala | Tyr | Cys |
| | 50 | | | | | 55 | | | | | 60 | | | | |

| Gly | Gly | Ile | Tyr |
| 65 | | | |

( 2 ) INFORMATION FOR SEQ ID NO:48:

( i ) SEQUENCE CHARACTERISTICS:
        ( A ) LENGTH: 68 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Conus magus ( x i ) SEQUENCE DESCRIPTION: SEQ ID NO:48:

```
Met Gly Met Arg Met Met Phe Thr Val Phe Leu Leu Val Val Leu Ala
 1               5                  10                  15
Thr Thr Val Val Ser Phe Pro Ser Asp Arg Ala Ser Asp Gly Arg Asn
            20                  25                  30
Ala Ala Ala Asn Asp Lys Ala Ser Asp Val Ile Thr Leu Ala Leu Lys
         35                  40                  45
Gly Cys Cys Ser Asn Pro Val Cys His Leu Glu His Ser Asn Leu Cys
     50                  55                  60
Gly Arg Arg Arg
 65
```

( 2 ) INFORMATION FOR SEQ ID NO:49:

( i ) SEQUENCE CHARACTERISTICS:
        ( A ) LENGTH: 70 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Conus sulcatus ( x i ) SEQUENCE DESCRIPTION: SEQ ID NO:49:

```
Met Gly Met Arg Met Met Phe Thr Val Phe Leu Leu Val Val Leu Ala
 1               5                  10                  15
Thr Thr Val Val Ser Phe Asn Ser Asp Arg Asp Pro Ala Leu Gly Gly
            20                  25                  30
Arg Asn Ala Ala Ala Ile Ala Ser Asp Lys Ile Ala Ser Thr Leu Arg
         35                  40                  45
Arg Gly Gly Cys Cys Ser Phe Pro Ala Cys Arg Lys Tyr Arg Pro Glu
     50                  55                  60
Met Cys Gly Gly Arg Arg
 65              70
```

( 2 ) INFORMATION FOR SEQ ID NO:50:

( i ) SEQUENCE CHARACTERISTICS:
        ( A ) LENGTH: 62 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO (vi) ORIGINAL SOURCE:
    (A) ORGANISM: Conus caracteristicus (xi) SEQUENCE DESCRIPTION: SEQ ID NO:50:

Met Gly Met Arg Met Met Phe Thr Val Phe Leu Leu Val Val Leu Ala
1               5                   10                  15
Thr Thr Val Val Ser Phe Thr Ser Asp Arg Ala Ser Asp Gly Arg Asn
            20                  25                  30
Ala Ala Ala Asn Ala Phe Asp Leu Ile Ala Leu Ile Ala Arg Gln Asn
        35                  40                  45
Cys Cys Ser Ile Pro Ser Cys Trp Glu Lys Tyr Lys Cys Ser
    50                  55                  60

(2) INFORMATION FOR SEQ ID NO:51:

(i) SEQUENCE CHARACTERISTICS:
       (A) LENGTH: 62 amino acids
       (B) TYPE: amino acid
       (C) STRANDEDNESS:
       (D) TOPOLOGY: linear (ii) MOLECULE TYPE: peptide (iii) HYPOTHETICAL: NO (vi) ORIGINAL SOURCE:
        (A) ORGANISM: Conus bandanus (xi) SEQUENCE DESCRIPTION: SEQ ID NO:51:

Met Gly Met Arg Met Met Phe Thr Val Phe Leu Leu Val Val Leu Ala
1               5                   10                  15
Thr Ala Val Leu Pro Val Thr Leu Asp Arg Ala Ser Asp Gly Arg Asn
            20                  25                  30
Ala Ala Ala Asn Ala Lys Thr Pro Arg Leu Ile Ala Pro Phe Ile Arg
        35                  40                  45
Asp Tyr Cys Cys His Arg Gly Pro Cys Met Val Trp Cys Gly
    50                  55                  60

(2) INFORMATION FOR SEQ ID NO:52:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Conus geographus (xi) SEQUENCE DESCRIPTION: SEQ ID NO:52:

TCTGCGAATG GGCATGCGGA TGATGTT         27

(2) INFORMATION FOR SEQ ID NO:53:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (genomic)

(  i i i  ) HYPOTHETICAL: NO (  i v  ) ANTI-SENSE: YES (  v i  ) ORIGINAL SOURCE:
        ( A ) ORGANISM: Conus geographus (  x i  ) SEQUENCE DESCRIPTION: SEQ ID NO:53:

TGCTCCAACG TCGTGGTTCA GAGGGTC          27

( 2 ) INFORMATION FOR SEQ ID NO:54:

(  i  ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear (  i i  ) MOLECULE TYPE: peptide (  i i i  ) HYPOTHETICAL: NO (  v i  ) ORIGINAL SOURCE:
        ( A ) ORGANISM: Conus magus (  i x  ) FEATURE:
        ( A ) NAME/KEY: Modified-site
        ( B ) LOCATION: 16
        ( D ) OTHER INFORMATION: /note= "The C-terminus is
            amidated."

(  x i  ) SEQUENCE DESCRIPTION: SEQ ID NO:54:

Gly Cys Cys Ser Asn Pro Val Cys His Leu Glu His Ser Asn Leu Cys
1             5                             10                       15

( 2 ) INFORMATION FOR SEQ ID NO:55:

(  i  ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear (  i i  ) MOLECULE TYPE: peptide (  i i i  ) HYPOTHETICAL: NO (  v i  ) ORIGINAL SOURCE:
        ( A ) ORGANISM: Conus striatus (  x i  ) SEQUENCE DESCRIPTION: SEQ ID NO:55:

Gly Cys Cys Cys Asn Pro Ala Cys Gly Pro Asn Tyr Gly Cys Gly Thr
1             5                             10                       15

Ser Cys Ser Arg Thr Leu
            20

( 2 ) INFORMATION FOR SEQ ID NO:56:

(  i  ) SEQUENCE CHARACTERISTICS:
        ( A ) LENGTH: 42 amino acids
        ( B ) TYPE: amino acid
        ( C ) STRANDEDNESS:
        ( D ) TOPOLOGY: linear (  i i  ) MOLECULE TYPE: peptide (  i i i  ) HYPOTHETICAL: NO (  v i  ) ORIGINAL SOURCE:
        ( A ) ORGANISM: Conus striatus (  x i  ) SEQUENCE DESCRIPTION: SEQ ID NO:56:

```
    Gln  Lys  Glu  Leu  Val  Pro  Ser  Val  Ile  Thr  Thr  Cys  Cys  Gly  Tyr  Asp
    1              5                        10                       15

Pro  Gly  Thr  Met  Cys  Pro  Pro  Cys  Arg  Cys  Thr  Asn  Ser  Cys  Pro  Thr
                   20                       25                       30

Lys  Pro  Lys  Lys  Pro  Gly  Arg  Arg  Asn  Asp
              35                  40
```

( 2 ) INFORMATION FOR SEQ ID NO:57:

( i ) SEQUENCE CHARACTERISTICS:
        ( A ) LENGTH: 41 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Conus magus ( x i ) SEQUENCE DESCRIPTION: SEQ ID NO:57:

```
    Ala  Pro  Glu  Leu  Val  Val  Thr  Ala  Thr  Thr  Asn  Cys  Cys  Gly  Tyr  Asn
    1              5                        10                       15

Pro  Met  Thr  Ile  Cys  Pro  Pro  Cys  Met  Cys  Thr  Tyr  Ser  Cys  Pro  Pro
                   20                       25                       30

Lys  Arg  Lys  Pro  Gly  Arg  Arg  Asn  Asp
              35                  40
```

( 2 ) INFORMATION FOR SEQ ID NO:58:

( i ) SEQUENCE CHARACTERISTICS:
        ( A ) LENGTH: 42 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Conus stercusmuscarum ( x i ) SEQUENCE DESCRIPTION: SEQ ID NO:58:

```
    Glx  Thr  Trp  Leu  Val  Pro  Ser  Thr  Ile  Thr  Thr  Cys  Cys  Gly  Tyr  Asp
    1              5                        10                       15

Pro  Gly  Thr  Met  Cys  Pro  Thr  Cys  Met  Cys  Asp  Asn  Thr  Cys  Lys  Pro
                   20                       25                       30

Lys  Pro  Lys  Lys  Ser  Gly  Arg  Arg  Asn  Asp
              35                  40
```

( 2 ) INFORMATION FOR SEQ ID NO:59:

( i ) SEQUENCE CHARACTERISTICS:
        ( A ) LENGTH: 42 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Conus stercusmuscarum ( x i ) SEQUENCE DESCRIPTION: SEQ ID NO:59:

| Ala | Pro | Trp | Leu | Val | Pro | Ser | Thr | Ile | Thr | Thr | Cys | Cys | Gly | Tyr | Asp |
|---|---|---|---|---|---|---|---|---|---|---|---|---|---|---|---|
| 1 | | | | 5 | | | | | 10 | | | | | 15 | |

| Pro | Gly | Ser | Met | Cys | Pro | Pro | Cys | Met | Cys | Asn | Asn | Thr | Cys | Lys | Pro |
|---|---|---|---|---|---|---|---|---|---|---|---|---|---|---|---|
| | | | 20 | | | | | 25 | | | | | 30 | | |

| Lys | Pro | Lys | Lys | Ser | Gly | Arg | Arg | Asn | His |
|---|---|---|---|---|---|---|---|---|---|
| | | 35 | | | | | 40 | | |